(12) United States Patent
Dunican et al.

(10) Patent No.: US 7,504,242 B2
(45) Date of Patent: *Mar. 17, 2009

(54) **PROCESS FOR THE FERMENTATIVE PRODUCTION OF AMINO ACIDS USING *CORYNEFORM* BACTERIA IN WHICH OPCA GENE EXPRESSION IS AMPLIFIED**

(75) Inventors: L. K. Dunican, County Galway (IE); Rita Dunican, legal representative, Galway (IE); Ashling McCormack, County Westmeath (IE); Cliona Stapelton, County Tipparary (IE); Kevin Burke, County Galway (IE)

(73) Assignee: Evonik Degussa GmbH, Essen (DE)

( * ) Notice: Subject to any disclaimer, the term of this patent is extended or adjusted under 35 U.S.C. 154(b) by 319 days.

This patent is subject to a terminal disclaimer.

(21) Appl. No.: 10/976,768

(22) Filed: Nov. 1, 2004

(65) Prior Publication Data

US 2005/0112730 A1 May 26, 2005

Related U.S. Application Data

(60) Division of application No. 10/137,655, filed on May 3, 2002, now Pat. No. 6,825,029, which is a continuation-in-part of application No. 09/531,267, filed on Mar. 20, 2000, now abandoned.

(60) Provisional application No. 60/142,915, filed on Jul. 9, 1999.

(51) Int. Cl.
*C12P 13/04* (2006.01)
*C12P 13/08* (2006.01)
*C12P 13/02* (2006.01)
*C12P 13/06* (2006.01)
*C12N 9/12* (2006.01)
*C12N 15/00* (2006.01)
*C12N 1/21* (2006.01)
*C12N 5/10* (2006.01)
*C12P 21/06* (2006.01)
*C12Q 1/48* (2006.01)
*C07K 14/00* (2006.01)
*C07H 21/00* (2006.01)

(52) U.S. Cl. ............... 435/106; 435/108; 435/115; 435/116; 435/320.1; 435/252.32; 435/194; 435/69.1; 435/325; 435/15; 536/23.2; 530/350

(58) Field of Classification Search ............. 435/194, 435/69.1, 320.1, 252.32, 325, 15, 115, 108, 435/116; 536/23.2; 530/350

See application file for complete search history.

(56) References Cited

U.S. PATENT DOCUMENTS 6,962,989 B1 * 11/2005 Pompejus et al. ......... 536/23.7

FOREIGN PATENT DOCUMENTS

| EP | 1 108 790 | 6/2001 |
| JP | 9224 661 | 9/1997 |
| WO | WO 01/00844 | 1/2001 |

OTHER PUBLICATIONS

EMBL:E13655, Hatakeyama et al., "gDNA encoding glucose-6-phosphate dehydrogenase," June 23, 1998.

Derwent Abstract, Katsumata, R. et al., "L-Glutamic acid production by culturing *Corynebacterium* or *Brevibacterium* transformed with recombinant DNA containing information for production of phospho-fructo:kinase," May 7, 1988.

Kobayashi, et al., "Purification and Properties of NAD-Dependent D-Glucose Dehydrogenase Produced by Alkalophilic *Corynebacterium* sp. No. 93-1," Agricultural and Biological Chemistry, vol. 44, No. 10, 1980, pp. 2261-2269.

Newman, J. et al., "Synechococcus PCC7942 zwf region, fructose 1,6-biophosphatase (fbp), glucose 6-phosphate dehydrogenase (zwf), OpcA (opcA), cytochrome b6 (petD), and cytochrome b6f complex subunit IV (petB) genes, complete cds," FEMS Microbiology Letters, vol. 133, No. 1-2, 1995, pp. 187-193, Gen Bank U 33 285, Sep. 19, 1995.

Summers et al., "Transcriptional regulator of zwf, encoding glucose-6-phosphate dehydrogenase, from the cyanobacterium Nostoc punctiforme strain ATCC 29133," Molecular Microbiology, vol. 22, No. 3, 1996, pp. 473-480.

Sequence Alignment, GeneSeq. Accession No. AAT88030, Dec. 1997.

Sequence Alignment, SwissProt. Accession No. POR-AVESA, Apr. 1990.

Broun et al.. Science 282: 1315-1317, 1998.

Smith et al., Nature Biotechnology 15: 1222-1223, 1997.

Van de Loo et al, Proc. Natl. Acad. Sci. 92: 6743-6747, 1995.

Brenner, TIG 15: 132-1333, 1999.

Hagen, K. D. and J. C. Meeks (2001), "The unique cyanobacterial protein OpcA is an allosteric effector of glucose-6-phosphate dehydrogenase in Nostoc punctiforme ATCC 29133." J Biol Chem 276(15): 11477-86.

(Continued)

*Primary Examiner*—Delia M Ramirez
(74) *Attorney, Agent, or Firm*—Pillsbury Winthrop Shaw Pittman LLP

(57) ABSTRACT

The present invention relates to polynucleotides that encode proteins having OpcA enzymatic activity. These polynucleotides can be used for increasing lysine biosynthesis in *Coryneform glutamicum*.

22 Claims, 3 Drawing Sheets

OTHER PUBLICATIONS

Moritz, B., K. Striegel, et al. (2000). "Kinetic properties of the glucose-6-phosphate and 6-phosphogluconate dehydrogenases from *Corynebacterium glutamicum* and their application for predicting pentose phosphate pathway flux in vivo." Eur J Biochem 267(12): 3442-52.

Schaeffer, F. and R. Y. Stanier (1978). "Glucose-6-phosphate dehydrogenase of Anabaena sp. Kinetic and molecular properties." *Arch Microbiol* 116(1):9-19.

Sundaram, S., H. Karakaya, et al. (1998). "Multiple oligomeric forms of glucose-6-phosphate dehydrogenase in cyanobacteria and the role of OpcA in the assembly process." *Microbiology* 144 (Pt 6): 1549-56.

Summers, M. L. and J. C. Meeks (1996), "Transcriptional regulation of zwf, encoding glucose-6-phosphate dehydrogenase, from the *cyanobacterium* Nostoc punctiforme strain ATCC 29133." *Mol Microbiol* 22(3): 473-80.

* cited by examiner

PROCESS FOR THE FERMENTATIVE PRODUCTION OF AMINO ACIDS USING *CORYNEFORM* BACTERIA IN WHICH OPCA GENE EXPRESSION IS AMPLIFIED

CROSS REFERENCE TO RELATED APPLICATIONS

This is a divisional of U.S. patent application Ser. No. 10/137,655 filed May 3, 2002, now U.S. Pat. No. 6,825,029, which is a continuation-in-part application of U.S. patent application Ser. No. 09/531,267, filed Mar. 20, 2000, now abandoned, which claims priority to U.S. Provisional Application No. 60/142,915 filed Jul. 9, 1999. The contents of U.S. patent application Ser. No. 09/531,267 are incorporated herein by reference in their entirety.

FIELD OF THE INVENTION

The invention provides nucleotide sequences which code for the opcA gene and a process for the fermentative preparation of amino acids, in particular L-lysine using *coryneform* bacteria in which the opcA gene is amplified.

DESCRIPTION OF BACKGROUND ART

Amino acids, in particular L-lysine, are used in human medicine and in the pharmaceuticals industry, but in particular in animal nutrition.

It is known that amino acids are prepared by fermentation from strains of *coryneform* bacteria, in particular *Corynebacterium glutamicum*. Because of their great importance, work is constantly being undertaken to improve the preparation processes. Improvements to the processes can relate to fermentation measures, such as e.g. stirring and supply of oxygen, or the composition of the nutrient media, such as e.g. the sugar concentration during the fermentation, or the working up to the product form by e.g. ion exchange chromatography, or the intrinsic output properties of the microorganism itself.

Methods of mutagenesis, selection and mutant selection are used to improve the output properties of these microorganisms. Strains which are resistant to antimetabolites, such as e.g. the lysine analogue S-(2-aminoethyl)-cysteine, or are auxotrophic for metabolites of regulatory importance and produce L-amino acids, such as e.g. L-lysine, are obtained in this manner. Methods of the recombinant DNA technique have also been employed for some years for improving the strain of *Corynebacterium* strains which produce amino acids.

The importance of the pentose phosphate cycle for the biosynthesis is known.

Thus Oishi and Aida (Agricultural and Biological Chemistry 29, 83-89 (1965)) already report on the "hexose monophosphate shunt" of *Brevibacterium ammoniagenes*. Sugimoto and Shio (Agricultural and Biological Chemistry 51, 101-108 (1987)) report on the regulation of glucose 6-phosphate dehydrogenase in *Brevibacterium flavum*. Sugimoto and Shio (Agricultural and Biological Chemistry 51, 1257-11263 (1987)) report on the regulation of glucose 6-phosphate dehydrogenase in *Brevibacterium flavum*.

JP-A-09224661 discloses the nucleotide sequence of the glucose 6-phosphate dehydrogenase gene, called zwf, of *Brevibacterium flavum* MJ-223 (FERM BP-1497). JP-A-09224661 describes the N-terminal amino acid sequence of the Zwf polypeptide as Met Val Ile Phe Gly Val Thr Gly Asp Leu Ala Arg Lys Lys Leu.

However, it has not been possible to confirm this.

SUMMARY OF THE INVENTION

Amino acids, in particular L-lysine, are used in human medicine, in the pharmaceuticals industry and in particular in animal nutrition. There is therefore a general interest in providing new improved processes for the preparation of amino acids, in particular L-lysine.

When L-lysine or lysine are mentioned in the following, not only the base but also the salts, such as e.g. lysine monohydrochloride or lysine sulfate, are also meant by this.

The invention provides an isolated polynucleotide from *coryneform* bacteria, comprising at least one polynucleotide sequence chosen from the group consisting of a) polynucleotide which is identical to the extent of at least 70% to a polynucleotide which codes for polypeptides which comprise at least one of the amino acid sequences according to SEQ ID No. 3 or SEQ ID No. 5 or SEQ ID No. 8 or SEQ ID No. 10, b) polynucleotide which codes for polypeptides which comprise amino acid sequences which are identical to the extent of at least 70% to the amino acid sequences according to SEQ ID No.3 or SEQ ID No. 5 or according to SEQ ID No. 8 or SEQ ID No. 10, c) polynucleotide which is complementary to the polynucleotides of a) or b), or d) polynucleotide comprising at least 15 successive nucleotides of the polynucleotide sequences of a), b) or c).

The invention also provides the polynucleotide as described above, this polynucleotide preferably being a DNA which is capable of replication, comprising:

(i) one or more nucleotide sequence(s) chosen from the group consisting of SEQ ID No. 1, SEQ ID No. 4, SEQ ID No. 6, SEQ ID No. 9, or (ii) at least one sequence which corresponds to sequence (i) within the range of the degeneration of the genetic code, or (iii) at least one sequence which hybridizes with the sequence complementary to sequence (i) or (ii), and optionally (iv) sense mutations of neutral function in (i).

The invention also provides a polynucleotide comprising the nucleotide sequence as shown in SEQ ID No. 4 or SEQ ID No. 9, a polynucleotide which codes for a polypeptide which comprises at least one of the amino acid sequences as shown in SEQ ID No. 3, SEQ ID No. 5, SEQ ID No. 8 or SEQ ID No. 10, a vector containing the above polynucleotide, and *coryneform* bacteria, serving as the host cell, which contain the vector.

The invention also provides polynucleotides which substantially comprise a polynucleotide sequence, which are obtainable by screening by means of hybridization of a corresponding gene library, which comprises the complete gene with the polynucleotide sequence corresponding to SEQ ID No. 4 or SEQ ID No. 9, with a probe which comprises the sequence of the polynucleotide mentioned, according to SEQ ID No. 4 or SEQ ID No. 9 or a fragment thereof, and isolation of the DNA sequence mentioned.

BRIEF DESCRIPTION OF THE SEQUENCES

SEQ ID No. 1: DNA sequence isolated from *Corynebacterium glutamicum* ATCC13032.

SEQ ID No. 2: Amino acid sequence of the Zwf protein derived from SEQ ID No. 1.

SEQ ID No. 3: Amino acid sequence of the OpcA protein derived from SEQ ID No. 1.

SEQ ID No. 4: DNA sequence of the opcA gene of ATCC13032 taken from SEQ ID No. 1.

SEQ ID No. 5: Amino acid sequence of the OpcA protein derived from SEQ ID No. 4.

SEQ ID No. 6: DNA sequence isolated from *Corynebacterium glutamicum* ASO19.

SEQ ID No. 7: Amino acid sequence of the Zwf protein derived from SEQ ID No. 6.

SEQ ID No. 8: Amino acid sequence of the OpcA protein derived from SEQ ID No. 6.

SEQ ID No. 9: DNA sequence of the opcA gene of ASO19 taken from SEQ ID No. 6.

SEQ ID No. 10: Amino acid sequence of the OpcA protein derived from SEQ ID No. 9.

SEQ ID No. 11: Amino acid sequence of the N-terminus of the Zwf protein of the glucose 6-phosphate dehydrogenase from ATCC13032 which can be isolated.

SEQ ID No. 12: Amino acid sequence of the N-terminus of the OpcA protein of the glucose 6-phosphate dehydrogenase, which can be isolated from ATCC13032.

BRIEF DESCRIPTION OF THE FIGURES

Embodiments of the invention will be described with reference to the following Figures, in which the base pair numbers stated are approximate values obtained in the context of reproducibility, and in which.

DETAILED DESCRIPTION

Figure 1:
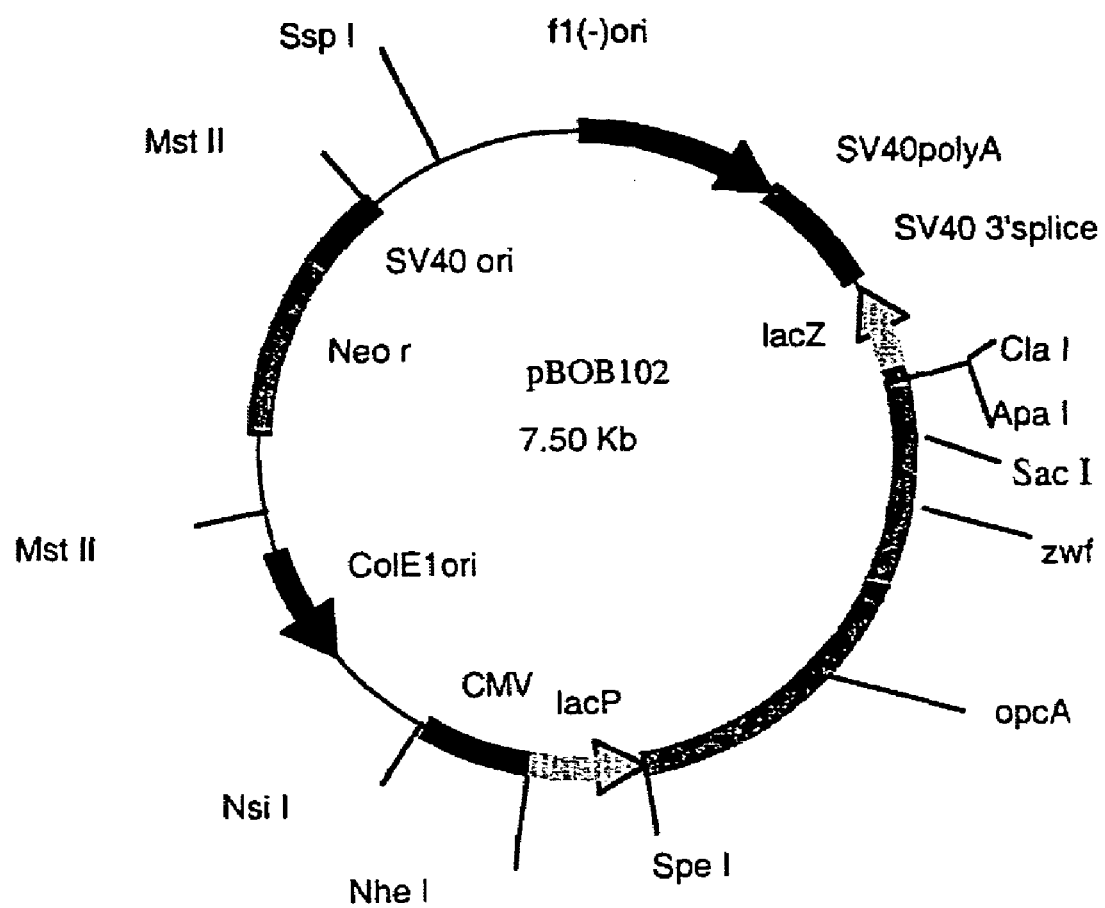
FIG. 1 is a map of the plasmid pBOB102.

Polynucleotide sequences according to the invention are suitable as hybridization probes for RNA, cDNA and DNA, in order to isolate, in the full length, cDNA which code for OpcA protein and to isolate those cDNA or genes which have a high similarity of sequence with that of the opcA gene.

Polynucleotide sequences according to the invention are furthermore suitable as primers for the preparation of DNA of genes which code for OpcA protein by the polymerase chain reaction (PCR).

Such oligonucleotides which serve as probes or primers comprise at least 30, preferably at least 20, especially preferably at lease 15 successive nucleotides. Oligonucleotides which have a length of at least 40 or 50 nucleotides are also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

"Polypeptides" is understood as meaning peptides or proteins which comprise two or more amino acids bonded via peptide bonds.

The polypeptides according to the invention include a polypeptide according to SEQ ID No. 3, SEQ ID No. 5, SEQ ID No. 8 or SEQ ID No. 10, in particular those with the biological activity of the OpcA gene product, and also those which are identical to the extent of at least 70% to the polypeptide according to SEQ ID No. 3, SEQ ID No. 5, SEQ ID No. 8 or SEQ ID No. 10, and preferably are identical to the extent of at least 80% and in particular to the extent of at least 90% to 95% to the polypeptide according to SEQ ID No. 3, SEQ ID No. 5, SEQ ID No. 8 or SEQ ID No. 10, and have the activity mentioned.

The invention also provides the new Zwf protein which forms the Zwf sub-unit of glucose 6-phosphate dehydrogenase. The amino acid sequence of the translation product is shown in SEQ ID no. 2 and SEQ ID No. 7. The N-terminal amino acid sequence of the Zwf sub-unit, which can be isolated, of glucose 6-phosphate dehydrogenase is shown in SEQ ID No. 11.

The invention also provides a process for the fermentative preparation of amino acids, in particular L-lysine, using *coryneform* bacteria which in particular already produce an amino acid, and in which the nucleotide sequences which code for the opcA gene are amplified, in particular over-expressed, optionally together with the zwf gene.

The term "amplification" in this connection describes the increase in the intracellular activity of one or more enzymes or proteins in a microorganism which are coded by the corresponding DNA, for example by increasing the number of copies of the gene or genes, using a potent promoter or using a gene or allele which codes for a corresponding enzyme or protein having a high activity, and optionally combining these measures.

By amplification measures, in particular over-expression, the activity or concentration of the corresponding enzyme or protein is in general increased by at least 10%, 25%, 50%, 75%, 100%, 150%, 200%, 300%, 400% or 500%, up to a maximum of 1000% or 2000%, based on that of the wild-type enzyme or protein or the activity or concentration of the enzyme or protein in the starting microorganism.

The microorganisms which the present invention provides can prepare L-amino acids, in particular L-lysine, from glucose, sucrose, lactose, fructose, maltose, molasses, starch, cellulose or from glycerol and ethanol. They can be representatives of *coryneform* bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum*, are, for example, the known wild-type strains

*Corynebacterium glutamicum* ATCC13032
*Corynebacterium acetoglutamicum* ATCC15806
*Corynebacterium acetoacidophilum* ATCC 13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and L-lysine-producing mutants or strains prepared therefrom, such as, for example

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464 and
*Corynebacterium glutamicum* DSM5715
*Corynebacterium glutamicum* DM58-1
*Corynebacterium glutamicum* DSM12866 and L-threonine-producing mutants or strains prepared therefrom, such as, for example

*Corynebacterium glutamicum* ATCC21649
*Brevibacterium flavum* BB69
*Brevibacterium flavum* DSM5399
*Brevibacterium lactofermentum* FERM-BP 269
*Brevibacterium lactofermentum* TBB-10 and L-isoleucine-producing mutants or strains prepared therefrom, such as, for example

*Corynebacterium glutamicum* ATCC 14309
*Corynebacterium glutamicum* ATCC 14310
*Corynebacterium glutamicum* ATCC 14311
*Corynebacterium glutamicum* ATCC 15168
*Corynebacterium ammoniagenes* ATCC 6871 and L-tryptophan-producing mutants or strains prepared therefrom, such as, for example

*Corynebacterium glutamicum* ATCC21850 and
*Corynebacterium glutamicum* KY9218(pKW9901).

The inventors have succeeded in isolating the new opcA gene of *C. glutamicum* which codes for the OpcA sub-unit of the enzyme glucose 6-phosphate dehydrogenase (EC 1.1.1.49).

To isolate the opcA gene or also other genes of *C. glutamicum*, a gene library of this microorganism is first set up in *E. coli*. The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990) or the handbook by Sambrook et al.: Molecular Cloning, A Laboratory Manual (Cold Spring Harbor Laboratory Press, 1989) may be mentioned as an example. A very well-known gene library is that of the *E. coli* K-12 strain W3110 set up in λ vectors by Kohara et al. (Cell 50, 495-508 (1987)). Bathe et al. (Molecular and General Genetics, 252:255-265, 1996) describe a gene library of *C. glutamicum* ATCC13032, which was set up with the aid of the cosmid vector SuperCos I (Wahl et al., 1987, Proceedings of the National Academy of Sciences USA, 84:2160-2164) in the *E. coli* K-12 strain NM554 (Raleigh et al., 1988, Nucleic Acids Research 16:1563-1575). Börmann et al. (Molecular Microbiology 6(3), 317-326)) (1992)) in turn describe a gene library of *C. glutamicum* ATCC13032 using the cosmid pHC79 (Hohn and Collins, Gene 11, 291-298 (1980)). O'Donohue (The Cloning and Molecular Analysis of Four Common Aromatic Amino Acid Biosynthetic Genes from *Corynebacterium glutamicum*. Ph.D. Thesis, National University of Ireland, Galway, 1997) describes the cloning of *C. glutamicum* genes using the λ Zap expression system described by Short et al. (Nucleic Acids Research, 16: 7583).

To prepare a gene library of *C. glutamicum* in *E. coli* it is also possible to use plasmids such as pBR322 (Bolivar, Life Sciences, 25, 807-818 (1979)) or pUC9 (Vieira et al., 1982, Gene, 19:259-268). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645-4649). The long DNA fragments cloned with the aid of cosmids can then in turn be subcloned and subsequently sequenced in the usual vectors which are suitable for sequencing, such as is described e.g. by Sanger et al. (Proceedings of the National Academy of Sciences of the United States of America, 74:5463-5467, 1977).

The DNA sequences obtained can then be investigated with known algorithms or sequence analysis programs, such as e.g. that of Staden (Nucleic Acids Research 14, 217-232 (1986)), the GCG program of Butler (Methods of Biochemical Analysis 39, 74-97 (1998)) the FASTA algorithm of Pearson and Lipman (Proceedings of the National Academy of Sciences USA 85,2444-2448 (1988)) or the BLAST algorithm of Altschul et al. (Nature Genetics 6, 119-129 (1994)) and compared with the sequence entries which exist in databanks accessible to the public. Databanks for nucleotide sequences which are accessible to the public are, for example, that of the European Molecular Biology Laboratories (EMBL, Heidelberg, Germany) or that of the National Center for Biotechnology Information (NCBI, Bethesda, Md., USA).

The invention provides a new DNA sequence of *C. glutamicum* which codes for the opcA gene and which is a constituent of the present invention as SEQ ID NO 1 and SEQ ID NO 4. The amino acid sequence of the corresponding protein has furthermore been derived from the present DNA sequence by the methods described above. The resulting amino acid sequence of the OpcA gene product is shown in SEQ ID NO 3 and SEQ ID NO 5. The molecular weight resulting from the amino acid sequence of the OpcA gene product is approx. 34.7 kilo Dalton (kDa).

SEQ ID NO 1 also shows the coding region of the zwf gene. The resulting amino acid sequence of the Zwf gene product is shown in SEQ ID NO 2. The molecular weight resulting from the amino acid sequence of the Zwf gene product is approx. 57.5 kilo Dalton.

A gene library produced in the manner described above can furthermore be investigated by hybridization with nucleotide probes of known sequence, such as, for example, the zwf gene (JP-A-09224661). The cloned DNA of the clones which show a positive reaction in the hybridization is sequenced in turn to give on the one hand the known nucleotide sequence of the probe employed and on the other hand the adjacent new DNA sequences.

The invention also provides a new DNA sequence of *C. glutamicum* which codes for the opcA gene and which is a constituent of the present invention as SEQ ID NO 6 and SEQ ID NO 9. The amino acid sequence of the corresponding protein has furthermore been derived from the present DNA sequence by the methods described above. The resulting amino acid sequence of the OpcA gene product is shown in SEQ ID NO 8 and SEQ ID NO 10. The molecular weight resulting from the amino acid sequence of the OpcA gene product is approx. 34.7 kilo Dalton.

SEQ ID NO 6 also shows the coding region of the zwf gene. The resulting amino acid sequence of the Zwf gene product is shown in SEQ ID NO 7. The molecular weight resulting from the amino acid sequence of the Zwf gene product is approx. 57.5 kilo Dalton.

Another procedure for at least partly determining the amino acid sequence of the OpcA protein and the Zwf protein comprises purifying the glucose 6-phosphate dehydrogenase enzyme protein to homogeneity by chromatographic methods. Methods and instructions for protein purification and preparation are described e.g. in the textbook by Schleifer and Wensink: Practical Methods in Molecular Biology (Springer Verlag, Berlin, Germany, 1981), in the handbook by Harris and Angal: Protein Purification Methods: A Practical Approach (IRL Press, Oxford, UK, 1989), in the textbook by Scopes: Protein Purification: Principles and Practice, 3$^{rd}$ ed. (Springer Verlag, New York, USA, 1993) and in generally known textbooks and handbooks. The N-terminal amino acid sequence of the purified polypeptides can be determined by the method of N-terminal sequencing described by Edman (Archives of Biochemistry 22, 475 (1949)). Further methods and instructions for protein sequencing are described e.g. in Smith: Protein Sequencing Protocols: Methods in Molecular Biology, Vol. 64 and Vol. 112 (Humana Press, Totowa, N.J., USA, 1996) and in Kamp et al.: Protein Structure Analysis: Preparation, Characterization, and Microsequencing (Springer Verlag, New York, N.Y., USA, 1997).

It was possible to show in this manner that the enzyme glucose 6-phosphate dehydrogenase consists of two sub-units with in each case a molecular weight of approx. 30 kDa and approx. 60 kDa. The N-terminal amino acid sequence of the OpcA sub-unit and of the OpcA protein is shown in SEQ-ID-NO. 12. The N-terminal amino acid sequence of the Zwf sub-unit and of the Zwf protein is shown in SEQ-ID-NO. 11.

Coding DNA sequences which result from SEQ ID NO 1, SEQ ID NO 4, SEQ ID NO 6 or SEQ ID NO 9 by the degeneracy of the genetic code are also a constituent of the invention. In the same way, DNA sequences which hybridize with SEQ ID NO 4 or SEQ ID NO 9 or parts of SEQ ID NO 4 or SEQ ID NO 9 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751-757 (1987)), in O'Regan et al. (Gene 77:237-251 (1989)), in Sahin-Toth et al. (Protein Sciences 3:240-247 (1994)), in Hochuli et al. (Bio/Technology 6:1321-1325 (1988)) and in known textbooks of genetics and molecular biology. Amino acid sequences which result in a corresponding manner from SEQ ID NO 3, SEQ ID NO 5, SEQ ID NO 8 or SEQ ID NO 10 are also a constituent of the invention.

Finally, DNA sequences which are prepared by the polymerase chain reaction (PCR) using primers which result from SEQ ID NO 4 or SEQ ID NO 9 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255-260). Instructions for amplification of DNA sequences with the aid of the polymerase chain reaction (PCR) can be found by the expert, inter alia, in the handbook by Gait: Oligonucleotide synthesis: a practical approach (IRL Press, Oxford, UK, 1984) and in Newton and Graham: PCR (Spektrum Akademischer Verlag, Heidelberg, Germany, 1994).

The inventors have found that *coryneform* bacteria produce amino acids, in particular L-lysine, in an improved manner after over-expression of the opcA gene, optionally together with the zwf gene.

The use of endogenous genes in particular endogenous genes from *coryneform* bacteria is preferred. "Endogenous genes" or "endogenous nucleotide sequences" refer to genes, alleles or nucleotide sequences which are available in the population of a species.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-lysine production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in European Patent Specification EPS 0 472 869, in U.S. Pat. No. 4,601,893, in Schwarzer and Pühler (Bio/Technology 9, 84-87 (1991)), in Reinscheid et al. (Applied and Environmental Microbiology 60, 126-132 (1994)), in LaBarre et al. (Journal of Bacteriology 175, 1001-1007 (1993)), in Patent Application WO 96/15246, in Malumbres et al. (Gene 134, 15-24 (1993)), in Japanese Laid-Open Specification JP-A-10-229891, in Jensen and Hammer (Biotechnology and Bioengineering 58, 191-195 (1998)), in Makrides (Microbiological Reviews 60:512-538 (1996)) and in known textbooks of genetics and molecular biology.

By way of example, the opcA gene according to the invention was over-expressed with the aid of plasmids.

Suitable plasmids are those which are replicated in *coryneform* bacteria. Numerous known plasmid vectors, such as e.g pZ1 (Menkel et al., Applied and Environmental Microbiology (1989) 64: 549-554), pEKEx1 (Eikmanns et al., Gene 102: 93-98 (1991)) or pHS2-1 (Sonnen et al., Gene 107:69-74 (1991)) are based on the cryptic plasmids pHM1519, pBL1 or pGA1. Other plasmid vectors, such as e.g. those based on pCG4 (U.S. Pat. No. 4,489,160), or pNG2 (Serwold-Davis et al., FEMS Microbiology Letters 66, 119-124 (1990)), or pAG1 (U.S. Pat. No. 5,158,891), can be used in the same manner.

Figure 2:
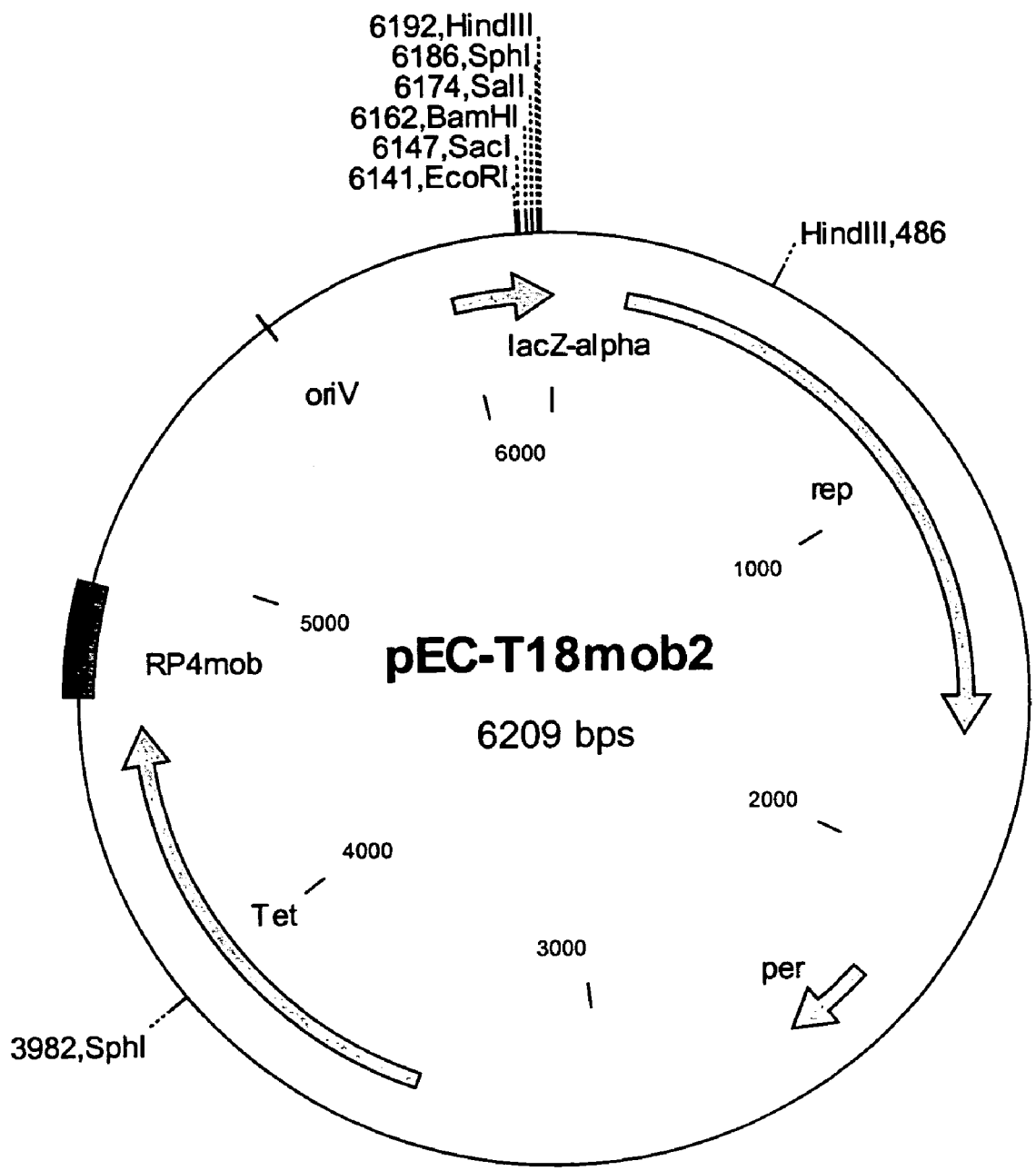
FIG. 2 is a map of the plasmid pEC-T18mob2.

The E. coli—C. glutamicum shuttle vector pEC-T18mob2 shown in FIG. 2 was used as an example. After incorporation of the opcA gene and the zwf gene into the SphI/SalI cleavage site region of pEC-T18mob2, the plasmid pECzwfopcA shown in FIG. 3 was formed.

Plasmid vectors which are furthermore suitable are also those with the aid of which the process of gene amplification by integration into the chromosome can be used, as has been described, for example, by Reinscheid et al. (Applied and Environmental Microbiology 60, 126-132 (1994)) for duplication or amplification of the hom-thrB operon. In this method, the complete gene is cloned in a plasmid vector which can replicate in a host (typically E. coli), but not in C. glutamicum. Possible vectors are, for example, pSUP301 (Simon et al., Bio/Technology 1, 784-791 (1983)), pK18mob or pK19mob (Schäfer et al., Gene 145, 69-73 (1994)), pGEM-T (Promega Corporation, Madison, Wis., USA), pCR2.1-TOPO (Shuman (1994). Journal of Biological Chemistry 269:32678-84; U.S. Pat. No. 5,487,993), pCR®Blunt (Invitrogen, Groningen, Holland; Bernard et al., Journal of Molecular Biology, 234: 534-541 (1993)), pEM1 (Schrumpf et al, 1991, Journal of Bacteriology 173:4510-4516) or pBGS8 (Spratt et al.,1986, Gene 41: 337-342). The plasmid vector which contains the gene to be amplified is then transferred into the desired strain of C. glutamicum by conjugation or transformation. The method of conjugation is described, for example, by Schäfer et al. (Applied and Environmental Microbiology 60, 756-759 (1994)). Methods for transformation are described, for example, by Thierbach et al. (Applied Microbiology and Biotechnology 29, 356-362 (1988)), Dunican and Shivnan (Bio/Technology 7, 1067-1070 (1989)) and Tauch et al. (FEMS Microbiological Letters 123, 343-347 (1994)). After homologous recombination by means of a "cross over" event, the resulting strain contains at least two copies of the gene in question.

In addition, it may be advantageous for the production of amino acids, in particular L-lysine, to amplify or over-express one or more enzymes of the particular biosynthesis pathway, of glycolysis, of anaplerosis, of the pentose phosphate pathway or of amino acid export, in addition to the opcA gene, optionally together with the zwf gene.

Thus, for example, for the preparation of L-lysine, it may be advantageous for one or more genes chosen from the group consisting of the dapA gene which codes for dihydrodipicolinate synthase (EP-B 0 197 335), the lysC gene which codes for a feed back resistant aspartate kinase (Kalinowski et al. (1990), Molecular and General Genetics 224: 317-324), the gap gene which codes for glycerolaldehyde 3-phosphate dehydrogenase (Eikmanns (1992), Journal of Bacteriology 174:6076-6086), the pyc gene which codes for pyruvate carboxylase (DE-A-198 31 609), the tkt gene which codes for transketolase (accession number AB023377 of the databank of European Molecular Biology Laboratories (EMBL, Heidelberg, Germany)), the gnd gene which codes for 6-phosphogluconate dehydrogenase (JP-A-9-224662), the lysE gene which codes for the lysine export protein (DE-A-195 48 222), the zwa1 gene (DE 199 59 328.0; DSM 13115), or the eno gene which codes for enolase (DE: 199 41 478.5), the tal gene which codes for transaldolase (DSM 13263)

to be amplified, in particular over-expressed, at the same time. The use of endogenous genes in particular endogenous genes from *coryneform* bacteria is preferred.

It may furthermore be advantageous for the production of amino acids, in particular L-lysine, at the same time to attenuate the pck gene which codes for phosphoenol pyruvate carboxykinase (DE 199 50 409.1 DSM 13047) and/or the pgi gene which codes for glucose 6-phosphate isomerase (U.S. Ser. No. 09/396,478, DSM 12969), or the poxB gene which codes for pyruvate oxidase (DE 199 51 975.7; DSM 13114), or the zwa2 gene (DE: 199 59 327.2; DSM 13113)

in addition to the amplification of the opcA gene, optionally in combination with the zwf gene.

In this connection, the term "attenuation" means reducing or suppressing the intracellular activity or concentration of one or more enzymes or proteins in a microorganism, which enzymes or proteins are coded by the corresponding DNA, for example by using a weak promoter or a gene or allele which codes for a corresponding enzyme or protein which has a low activity or inactivates the corresponding enzyme or protein and optionally by combining these measures.

By attenuation measures, the activity or concentration of the corresponding enzyme or protein is in general reduced to 0 to 75%, 0 to 50%, 0 to 25%, 0 to 10% or 0 to 5% of the activity or concentration of the wild-type enzyme or protein or of the activity or concentration of the enzyme or protein in the starting microorganism.

In addition to over-expression of the opcA gene it may furthermore be advantageous for the production of amino acids, in particular L-lysine, to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms prepared according to the invention can be cultured continuously or discontinuously in the batch process (batch culture) or in the fed batch (feed process) or repeated fed batch process (repetitive feed process) for the purpose of production of L-amino acids, in particular L-lysine. A summary of known culture methods are described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substance can be used individually or as a mixture. Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture. Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of L-amino acid has formed. This target is usually reached within 10 hours to 160 hours.

The analysis of L-amino acids can be carried out by anion exchange chromatography with subsequent ninhydrin derivation, as described by Spackman et al. (Analytical Chemistry, 30, (1958), 1190).

The following microorganism was deposited at the Deutsche Sammlung für Mikroorganismen und Zellkulturen Mascheroder Weg 1B, D-3300, Braunschweig, Germany on Jan. 26, 2000 in accordance with the Budapest Treaty:

*Corynebacterium glutamicum* ATCC13032/pECzwfopcA under accession number DSM13264.

SEQ ID NO 1 also contains the new devB gene. The process according to the invention is used for the fermentative preparation of amino acids, in particular L-lysine.

With reference to FIG. 1, the abbreviations that are used have the following meanings:
Neo r: Neomycin/kanamycin resistance
ColE1 ori: origin of replication of plasmid ColE1
CMV: Cytomegalovirus promoter
lacP: promotor of lac operon
lacZ: 5'-end of β-galactosidase gene (lacZa gene fragment)
SV40 3' splice 3' splice site of Simian Virus 40
SV40 polyA: polyadenylation site of Simian Virus 40
fl(-)ori: origin of replication of filamentousphage fl
SV40 ori: origin of replication of Simian Virus 40

Figure 3:
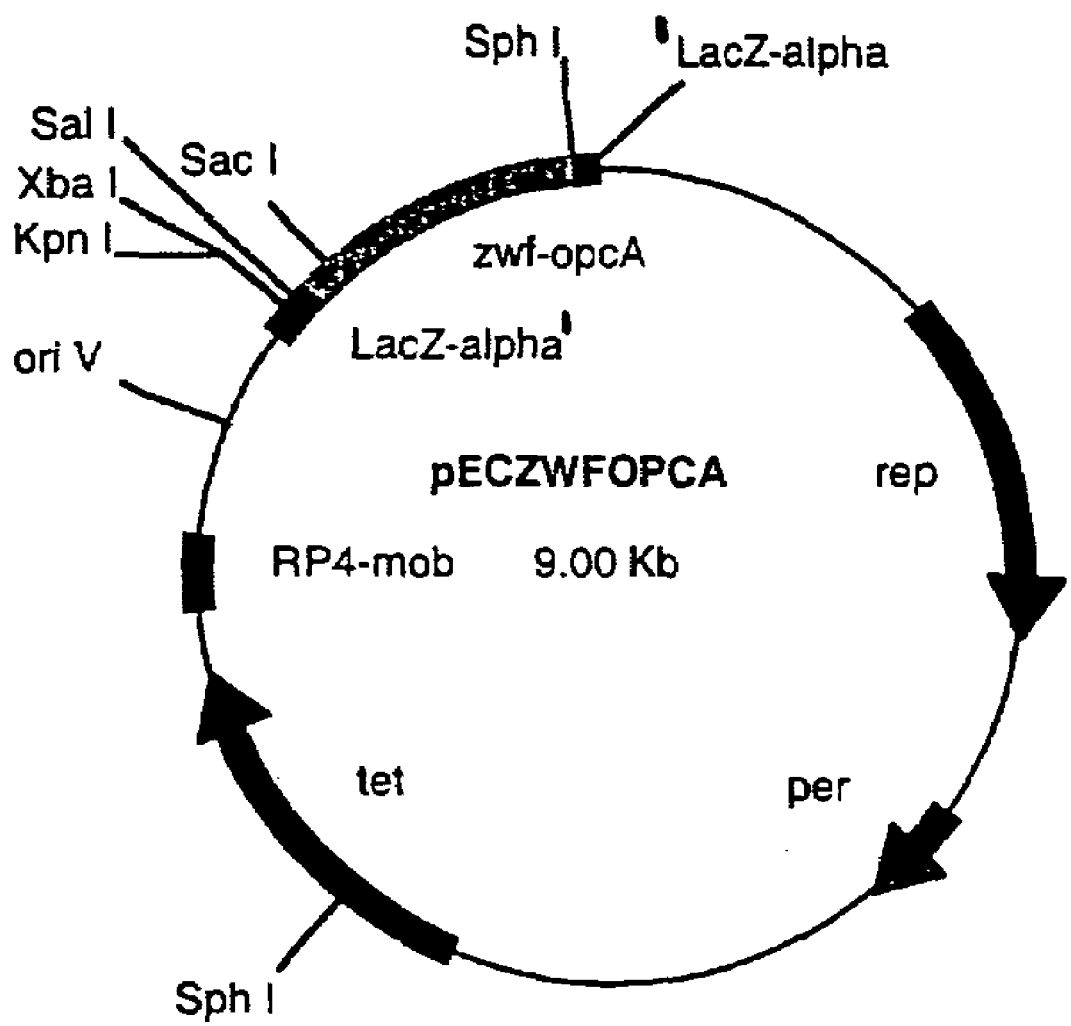
FIG. 3 is a map of the plasmid pECzwfopcA.

With reference to FIGS. 2 and 3, the abbreviations that are used have the following meanings:
Tet: Resistance gene for tetracycline
oriV: Plasmid-coded replication origin of *E. coli*
RP4mob: mob region for mobilizing the plasmid
rep: Plasmid-coded replication origin from *C. glutamicum* plasmid pGA1
per: Gene for controlling the number of copies from PGA1
lacZ-alpha: lacZα gene fragment (N-terminus) of the β-galactosidase gene
lacZalpha': 5'-Terminus of the lacZα gene fragment
'lacZalpha: 3'-Terminus of the lacZα gene fragment
zwf: zwf gene
opcA: opcA gene Certain other abbreviations are also used in the Figures, as follows:
ApaI: cleavage site of restriction enzyme ApaI
BamHI: cleavage site of restriction enzyme BamHI
ClaI: cleavage site of restriction enzyme ClaI
EcoRI: cleavage site of restriction enzyme EcoRI
HindIII: cleavage site of restriction enzyme HindIII
MstII: cleavage site of restriction enzyme MstII
NheI: cleavage site of restriction enzyme NheI
NsiI: cleavage site of restriction enzyme NsiI
SacI: cleavage site of restriction enzyme SacI
SalI: cleavage site of restriction enzyme SalI
SpeI: cleavage site of restriction enzyme SpeI
SphI: cleavage site of restriction enzyme SphI
SspI: cleavage site of restriction enzyme SspI
XbaI: cleavage site of restriction enzyme XbaI The following examples will further illustrate this invention. The molecular biology techniques, e.g. plasmid DNA isolation, restriction enzyme treatment, ligations, standard transformations of *Escherichia coli* etc. used are, (unless stated otherwise), described by Sambrook et al., (Molecular Cloning. A Laboratory Manual (1989) Cold Spring Harbor Laboratories, USA).

EXAMPLE 1

Construction of a Gene Library of *Corynebacterium Glutamicum* Strain AS019

A DNA library of *Corynebacterium glutamicum* strain ASO19 (Yoshihama et al., Journal of Bacteriology 162, 591-597 (1985)) was constructed using λ Zap Express™ system, (Short et al., (1988) Nucleic Acids Research, 16: 7583-7600), as described by O'Donohue (O'Donohue, M. (1997). The Cloning and Molecular Analysis of Four Common Aromatic Amino Acid Biosynthetic Genes from *Corynebacterium glutamicum*. Ph.D. Thesis, National University of Ireland, Galway.). λ Zap Express™ kit was purchased from Stratagene (Stratagene, 11011 North Torrey Pines Rd., La Jolla, Calif. 92037.) and used according to the manufacturers instructions. AS019-DNA was digested with restriction enzyme Sau3A and ligated to BamHI treated and dephosphorylated λ Zap Express™ arms.

EXAMPLE 2

Cloning and Sequencing of the opcA and zwf Gene 2.1 Construction of a zwf Probe

A radio-labeled oligonucleotide, internal to the zwf gene, was used to probe the AS019 λ Zap Express™ library described above. The oligonucleotide was produced using degenerate PCR primers internal to the zwf gene. The degenerate nucleotide primers designed for the PCR amplification of zwf DNA fragments were as follows:

```
                                         (SEQ ID NO: 13)
zwf1:
5' ATY GAY CAC TAY YTS GGY AAR GA 3' zwf2:
5' RAA WGG MAC RCC YKS CCA 3'           (SEQ ID NO: 14)
``` with R=A+G; Y=C+T; W=A+T; M=A+C; S=G+C; K=T+G.

The estimated size of the resulting PCR product was 480 bp approximately.

Optimal PCR conditions were determined to be as follows:
  35 cycles
  94° C. for 1 minute
  60° C. for 1 minute
  72° C. for 30 seconds
  2.5-3.5 mM $MgCl_2$
  100-150 ng AS019 genomic DNA Sequence analysis of the resulting PCR product confirmed the product to be an internal portion of the zwf gene. Sequence analysis was carried out using the universal forward and reverse primers, and T7 sequencing kit from Pharmacia Biotech, (St. Albans, Herts, UK).

2.2 Cloning

Screening of the AS019 λ Zap Express™ library was carried out according to the λ Zap Express™ system protocol, (Stratagene, 11011 North Torrey Pines Rd., La Jolla, Calif. 92037.). Southern Blot analysis was then carried out on isolated clones. Southern transfer of DNA was as described in the Schleicher and Schuell protocols manual employing Nytran™ as membrane ("Nytran, Modified Nylon-66 Membrane Filters" (March 1987), Schleicher and Schuell, Dassel, Germany). Double stranded DNA fragments, generated using the same primers and optimal PCR conditions as described above, were radio-labeled with $\alpha$-$^{32}$P-dCTP using the Multiprime™ DNA labelling kit from Amershan Life Science (Amersham Pharmacia Biotech UK Limited, Little Chalfont, Buckinghamshire, UK) according to the manufacturers instructions.

Pre-hybridization, hybridization and washing conditions were as described in the Schleicher and Schuell protocols manual. Autoradiography was carried out according to the procedure outlined in the handbook of Sambrook et al. using AgFa Curix RPIL film. Thus several zwf clones were identified. Plasmid DNA was isolated from one of the clones, designated pBOB102 (FIG. 1) and chosen for further analysis.

2.3 Sequencing

The Sanger Dideoxy chain termination method of Sanger et al. (Proceedings of the National Academy of Sciences USA 74, 5463-5467 (1977)) was used to sequence the cloned insert of pBOB102. The method was applied using the T7 sequencing kit and α-$^{35}$S-dCTP from Pharmacia Biotech (St. Albans, Herts, UK). Samples were electrophoresed for 3-8 hours on 6% polyacrylamide/urea gels in TBE buffer at a constant current of 50 mA, according to the Pharmacia cloning and sequencing instructions manual ("$^{T7}$ Sequencing™ Kit", ref. XY-010-00-19, Pharmacia Biotech, 1994). Initial sequence analysis was carried out using the universal forward and M13 reverse primers obtained from Pharmacia Biotech:

```
                                        (SEQ ID NO: 15)
Universal forward primer:
5' GTA ATA CGA CTC ACT ATA GGG C 3'

M13 reverse primer:
5' GGA AAC AGC TAT GAC CAT G 3'        (SEQ ID NO: 16)
```

Internal primers were subsequently designed from the sequence obtained which allowed the entire opcA gene to be deduced. The sequences of the internal primers were as follows:

```
Internal primer 1:
5' TCA ACC CTG AGT CCA CC 3'           (SEQ ID NO: 17)

Internal primer 2:
5' CTG ACC ACG AGC GGA GG 3'           (SEQ ID NO: 18)

Internal primer 3:
5' ATG GTG ATC TGG ACG TG 3'           (SEQ ID NO: 19)

Internal primer 4:
5' CTG GCG ACT TGG CTC GA 3'           (SEQ ID NO: 20)

Internal primer 5:
5' CTT CCG GAT ACC ACC ACC 3'          (SEQ ID NO: 21)
```

Sequence obtained was then analyzed using the DNA Strider program, (Marck (1988), Nucleic Acids Research 16: 1829-1836), version 1.0 on an Apple Macintosh computer. This program allowed for analyses such as restriction site usage, open reading frame analysis and codon usage determination. Searches between DNA sequence obtained and those in EMBL and Genbank databases were achieved using the BLAST program, (Altschul et al., (1997) Nucleic Acids Research, 25: 3389-3402). DNA and protein sequences were aligned using the Clustal V and Clustal W programs (Higgins and Sharp, 1988 Gene 73: 237-244).

The sequence thus obtained is shown in SEQ ID NO 6. The analysis of the nucleotide sequence obtained revealed an open reading frame of 957 base pairs which was designated as opcA gene. It codes for a protein of 319 amino acids shown in SEQ ID NO 8 and SEQ ID NO 10. The coding region of the zwf gene is also shown in SEQ ID NO 6. The amino acid sequence of the Zwf-Protein composed of 514 amino acids is shown in SEQ ID NO 7.

EXAMPLE 3

Preparation of a Genomic Cosmid Gene Library from *Corynebacterium glutamicum* ATCC 13032

Chromosomal DNA from *Corynebacterium glutamicum* ATCC 13032 was isolated as described by Tauch et al. (1995, Plasmid 33:168-179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987) Proceedings of the National Academy of Sciences USA 84:2160-2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase. The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no. 27-0870-04). The ligation mixture was then packed in phages with the aid of Gigapack II XL Packing Extracts (Stratagene, La Jolla, USA, Product Description Gigapack II XL Packing Extract, Code no. 200217). For infection of the *E. coli* strain NM554 (Raleigh et al. 1988, Nucleic Acid Research 16:1563-1575) the cells were taken up in 10 mM $MgSO_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 µg/ml ampicillin. After incubation overnight at 37° C., recombinant individual clones were selected.

EXAMPLE 4

Isolation and Sequencing of the opcA and zwf Gene of ATCC 13032

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany). The DNA of the sequencing vector pZero-1, obtained from Invitrogen (Groningen, Holland, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol. Letters, 123:343-7) into the *E. coli* strain DH5αMCR (Grant, 1990, Proceedings of the National Academy of Sciences U.S.A., 87:4645-4649) and plated out on LB agar (Lennox, 1955, Virology, 1:190) with 50 µg/ml zeocin. The plasmid preparation of the recombinant clones was carried out with Biorobot 9600 (Product No. 900200, Qiagen, Hilden, Germany).

The sequencing was carried out by the dideoxy chain-stopping method of Sanger et al. (1977, Proceedings of the National Academy of Sciences U.S.A., 74:5463-5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217-231) version 97-0. The individual sequences of the pZero1 derivatives were assembled to a continuous contig. The computer-assisted coding region analysis were prepared with the XNIP program (Staden, 1986, Nucleic Acids Research, 14:217-231). Further analyses were carried out with the "BLAST search programs" (Altschul et al., 1997, Nucleic Acids Research, 25:3389-3402), against the non-redundant databank of the "National Center for Biotechnology Information" (NCBI, Bethesda, Md., USA).

The nucleotide sequence obtained is shown in SEQ ID NO 1. Analysis of the nucleotide sequence showed a coding region of 957 base pairs, which was called the opcA gene. The opcA gene, including its stop codon, is shown in SEQ ID NO 4. The opcA gene codes for a protein of 319 amino acids shown in SEQ ID NO 3 and SEQ ID NO 5.

EXAMPLE 5

Purification and N-Terminal Sequencing of the glucose-6-phosphate dehydrogenase of *Corynebacterium glutamicum* ATCC13032

5.1 Culture of strain ATCC 13032

For purification of the glucose-6-phosphate dehydrogenase *Corynebacterium glutamicum* ATCC 13032 was grown aerobically on minimal medium at 30° C. in a Labfors fermentation system (Infors AG, Bottmingen, Switzerland). A preculture (Bacto® Brain Heart Infusion medium, Difco Laboratories, Detroit, USA) was incubated for 15 hours at 30° C. and used for inoculation of 2.5 l minimal medium. The medium contained the following constituents (amounts per liter): 20 g $(NH_4)_2SO_4$; 1 g $KH_2PO_4$; 1 g $K_2HPO_4$; 0.25 g $MgSO_4 \times 7\ H_2O$; 10 mg $CaCl_2$; 0.2 mg biotin; 30 mg protocatechuic acid; 1 mg $FeSO_4 \times 7\ H_2O$; 1 mg $MnSO_4 \times H_2O$; 0.1 mg $ZnSO_4 \times 7\ H_2O$; 0.02 mg $CuSO_4$; 0.002 mg $NiCl_2 \times 6\ H_2O$; 1.2 g HCl; 0.2 g polypropylene glycol; 75 mg tritriplex II and 100 g glucose. During fermentation sodium hydroxide was continuously added in order to keep the pH-value constant at 7.0. The cells were harvested in the late exponential growth phase. After centrifugation using an Avanti J-25 centrifuge and a JA10 rotor of Beckman (Fullerton, USA) at 6400 g for 15 minutes at 4° C. and washing in 100 mM TRIS-HCl pH 7.5 containing 10 mM $MgCl_2$ the sediment was stored at −20° C. until use.

5.2 Enzyme Purification

Disruption of cells was carried out in a disintegration system (Disintegrator S, BIOmatic, Rodgau-Hainhausen, Germany). The cells were previously resuspended in a pH 7.5 buffer consisting of 100 mM TRIS-HCl, 10 mM $MgCl_2$, 0.75 mM DTT and a mixture of several protease inhibitors (complete™, Roche, Mannheim, Germany). The ratio of the cell wet weight to the total suspension weight was adjusted to 0.3.

After addition of 100 ml glass beads with a diameter of 0.1 to 0.25 mm (Fisher scientific, Düsseldorf, Germany) per 100 ml total suspension volume, cell disruption was performed at 5000 rpm for 12 Minutes. A temperature increase during disruption was prevented by ice cooling. After removal of glass beads an ultracentifugation step was carried through using an L8-70 M centrifuge and a Ti45 rotor of Beckman (Fullerton, USA) at 235000 g for 90 minutes at 4° C. The supernatant was used as crude extract for the purification of the glucose-6-phosphate dehydrogenase. All purification steps were carried out with a Biosys2000 system of Beckman (Fullerton, USA).

The crude extract was applied to an XK 50/30 column (Pharmacia, Freiburg, Germany), which contained Fractogel EMD DEAE-650(S) material (Merck, Darmstadt). The total bed volume was 500 ml. The column was previously equilibrated with 50 mM TRIS-HCl pH 7.5 containing 30 mM $MgCl_2$ and 0.75 mM DTT. After application of the crude extract the column was washed with the same buffer containing 144 mM KCl. Elution was performed within 95 minutes by a linear KCl gradient from 144 mM up to 320 mM. The flow rate was 7.4 ml/min. The active fractions were pooled and concentrated in centriprep® 30 concentrators (Amicon, Beverly, USA) using a Varifuge 3.0R centrifuge (Heraeus, Hanau, Germany) at 1500 g and 4° C. By dilution with 50 mM TRIS-HCl pH 7.5 containing 30 mM $MgCl_2$ and 0.75 mM DTT the KCl concentration was adjusted to 40 mM. After that the partially purified glucose-6-phosphate dehydrogenase was applied to an XK26/20 column (Pharmacia, Freiburg, Germany), which was filled with 65 ml Red-Sepharose CL6B (Pharmacia, Freiburg, Germany). The column was equilibrated with 50 mM TRIS-HCl pH 7.5 containing 30 mM $MgCl_2$ and 0.75 mM DTT. Elution was carried out within 590 minutes by a linear 0-800 mM KCl gradient at a flow rate of 0.87 ml/min.

After pooling of the active glucose-6-phosphate dehydrogenase fractions, the KCl concentration was reduced to 10 mM in the same way as described above. After that the solution was applied to an XK16/20 column (Pharmacia, Freiburg, Germany), which contained 20 ml of a 2'5'-ADP-sepharose matrix (Pharmacia, Freiburg, Germany). The column was equilibrated with the same buffer as the Red-Sepharose CL6B column. Elution was performed by an 0 to 2 mM NADP linear gradient. The active glucose-6-phosphate dehydrogenase-fractions were pooled and applied to a gel filtration column.

For gel filtration a Superdex G200pg column (Pharmacia, Freiburg, Germany) with a diameter of 1.6 cm and a bed volume of 114 ml was used. The elution at a flow rate of 1 ml/min was carried through with 50 mM TRIS-HCl pH 7.5 containing 30 mM $MgCl_2$, 200 mM KCl and 0.75 mM DTT. The active fractions were pooled and concentrated by ultrafiltration in centriprep® 30 concentrators (Amicon, Beverly, USA). After addition of 50% (v/v) glycerol to the purified glucose-6-phosphate dehydrogenase solution it was stored at −20° C.

During the whole purification process the glucose-6-phosphate-dehydrogenase activity and the protein concentration were measured.

The assay system for determination of the glucose-6-phosphate-dehydrogenase-activity contained 50 mM TRIS-HCl pH 7.5, 10 mM $MgCl_2$, 1 mM NADP and 200 mM potassium glutamate. The reaction was initiated by addition of 4 mM glucose-6-phosphate and the formation of NADPH was followed by measuring the increase in absorbance at 340 nm at 30° C. Protein concentrations were determined spectrophotometrically after Coomassie Brilliant Blue staining (Stoscheck, Methods in Enzymology 182, 50-68 (1990)). As protein standard bovine serum albumin was used. All measurements were carried out using a UV-160 A photometer (Shimadzu, Kyoto, Japan).

The purity of the glucose-6-phosphate dehydrogenase was tested by denaturing discontinuous SDS-gelelectrophoresis according to the method of Laemmli (Laemmli, U.K., Nature 227, 680-685 (1970)). After the third purification step using 2'5'-ADP sepharose ligand affinity material two different proteins with molecular weights of ca. 60 kDa and 30 kDa could be obtained. These two proteins could not be separated by gel filtration chromatography. The specific activity of this preparation was determined as 213 U/mg protein.

5.3 N-terminal Sequencing

N-terminal sequencing of the purified glucose-6-P dehydrogenase was performed according to the procedure of Edman (Edman and Begg, European Journal of Biochemistry 1, 80-91 (1967)) using a Procise® Protein Sequencing System (Applied Biosystems, Foster City, USA).

For the 60 kDa protein the following N-terminal sequence was obtained: Xaa Xaa Xaa Xaa Xaa Pro Xaa Xaa Trp Xaa Asn Pro Leu Arg Asp. It is also shown in SEQ ID No 11.

For the 30 kDa protein the following N-terminal sequence was obtained: Met Ile Phe Xaa Leu Pro Asp Xaa Xaa Xaa Gln Gln Ile Ser Lys. It is also shown in SEQ ID No 12.

EXAMPLE 6

Cloning of the zwf and opcA Genes into the pGEM T-Vector

PCR was used to amplify DNA fragments containing the entire zwf and opcA genes of *C. glutamicum* ATCC13032 and flanking upstream and downstream regions. PCR reactions were carried out using oligonucleotide primers designed from SEQ ID NO 1 and SEQ ID NO 6. Genomic DNA was isolated from *Corynebacterium glutamicum* ATCC13032 according to Heery and Dunican (Applied and Environmental Microbiology. 59: 791-799 (1993)) and used as template. The primers used were:

```
zwf fwd. primer:
5' AGA ATC AGC ACG CTG CAT CAG 3'    (SEQ ID NO: 22)

opcA rev. primer:
5' AGT ATG GTG CGC GTA CTA 3'        (SEQ ID NO: 23)
```

PCR parameters were as follows:
35 cycles
95° C. for 3 minutes
94° C. for 1 minute
47° C. for 1 minute
72° C. for 45 seconds
2.5 mM MgCl2
approx. 150-200 ng DNA template.

The PCR product obtained was cloned into the commercially available pGEM-T vector purchased from Promega Corp. (PGEM-T Easy Vector System 1, cat. no. A1360, Promega UK, Southampton) using *E. coli* strain JM109 (Yanisch-Perron et al., Gene 33: 103-119 (1985)) as a host.

EXAMPLE 7

Preparation of the Shuttle Vector pEC-T18Mob2

The *E. coli—C. glutamicum* shuttle vector pEC-T18mob2 was constructed according to the prior art.

The vector contains the replication region rep of the plasmid pGA1 including the replication effector per (U.S. Pat. No. 5,175,108; Nesvera et al., Journal of Bacteriology 179, 1525-1532 (1997)), the tetracycline resistance-imparting tetA(Z) gene of the plasmid pAG1 (U.S. Pat. No. 5,158,891; gene library entry at the National Center for Biotechnology Information (NCBI, Bethesda, Md., USA) with accession number AF121000), the replication region oriV of the plasmid pMB1 (Sutcliffe, Cold Spring Harbor Symposium on Quantitative Biology 43, 77-90 (1979)), the lacZα gene fragment including the lac promoter and a multiple cloning site (mcs) (Norrander et al. Gene 26, 101-106 (1983)) and the mob region of the plasmid RP4 (Simon et al., (1983) Bio/Technology 1:784-791).

The vector constructed was transformed in the *E. coli* strain DH5 α (Hanahan, In: DNA cloning. A practical approach. Vol. I. IRL-Press, Oxford, Washington D.C., USA). Selection for plasmid-carrying cells was made by plating out the transformation batch on LB agar (Sambrook et al., Molecular cloning: a laboratory manual. $2^{nd}$ Ed. Cold Spring Harbor Laboratory Press, Cold Spring Harbor, N.Y.), which had been supplemented with 5 mg/l tetracycline. Plasmid DNA was isolated from a transformant with the aid of the QIAprep Spin Miniprep Kit from Qiagen and checked by restriction with the restriction enzyme EcoRI and HindIII subsequent agarose gel electrophoresis (0.8%).

The plasmid was called pEC-T18mob2 and is shown in FIG. 2. It is deposited in the form of the strain *Escherichia coli* K-12 strain DH5α/pEC-T18mob2 at the Deutsche Sammlung für Mikroorganismen und Zellkulturen (DSMZ=German Collection of Microorganisms and Cell Cultures, Braunschweig, Germany) as DSM 13244.

EXAMPLE 8

Expression of glucose-6-phosphate dehydrogenase in *Corynebacterium glutamicum*

The entire zwf and opcA genes were subsequently isolated from the pGEM T-vector containing these genes (see Example 6) on an SphI/SalI fragment and cloned into the lacZα SphI/SalI sites of the *E. coli—C. glutamicum* shuttle vector pEC-T18mob2 (see Example 7 and FIG. 2). This shuttle vector contains two SphI sites. The first is situated within the multiple cloning site of lacZα and the second is situated within the gene conferring tetracycline resistance. Tetracycline (Sigma-Aldrich, PO Box 2424, Wimbome, Dorset BH21 7YR, UK) (5 mg/l) was used therefore as a selective pressure as only those clones containing the intact tetracycline resistance gene would grow. This new construct was designated pECzwfopcA (FIG. 3). Restriction enzyme analysis with SacI (Boehringer Mannheim GmbH, Germany) revealed the correct orientation of the zwf and opcA genes in the lacZα gene of pEC-T18mob2 i.e. downstream the lac promotor. *Corynebacterium glutamicum* ATCC13032 (American Type Culture Collection, Manasas, Va., USA) was transformed with this construct and electrotransfomnants were selected on Luria agar supplemented with isopropyl-thiogalactopyranoside (IPTG), 5-bromo-4-chloro-3-indolyl-galactopyranoside (XGAL) and tetracycline at concentrations of 1 mM, 0.02% and 5 mg/l respectively. Agar plates were incubated for 48 hours at 30° C. Rapid plasmid preparations were carried out as described by O'Gara and Dunican, (Applied and Environmental Microbiology 61: 4477-4479 (1995)), and Sac I restriction confirmed the presence of required clones. One of the clones was designated ATCC13032/pECzwfopcA.

EXAMPLE 9

Preparation of Amino Acid Producers with an Amplified opcA Gene

The L-lysine-producing strain *Corynebacterium glutamicum* DSM5715 is described in EP-B-0435132 and the L-threonine-producing strain *Brevibacterium flavum* DSM5399 is described in EP-B-0385940. Both strains are deposited at the Deutsche Sammlung für Mikroorganismen und Zellkulturen Mascheroder Weg 1B, D-3300, Braunschweig, Germany in accordance with the Budapest Treaty.

*Corynebacterium glutamicum* DSM5715 was deposited in the DSMZ in accordance with the Budapest Treaty on Dec. 22, 1989 under accession number DSM5715.

*Brevibacterium flavum* DSM5399 was deposited in the DSMZ in accordance with the Budapest Treaty on Jun. 26, 1989 under accession number DSM5399.

The strains DSM5715 and DSM5399 were transformed with the plasmid pECzwfopcA (Example 8) using the electroporation method described by Liebl et al., (FEMS Microbiology Letters, 53:299-303 (1989)) Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 5 mg/l tetracycline. Incubation was carried out for 2 days at 33° C.

The strains obtained in this way were called DSM5715/pECzwfopcA and DSM5399/pECzwfopcA.

EXAMPLE 10

Preparation of L-threonine

The *Brevibacterium flavum* strain DSM5399/pECzwfopcA obtained in Example 9 was cultured in a nutrient medium suitable for the production of threonine and the threonine content in the culture supernatant was determined.

For this, the strain was first incubated on an agar plate with the corresponding antibiotic (brain-heart agar with tetracycline (5 mg/l)) for 24 hours at 33° C. Starting from this agar plate culture, a preculture was seeded (10 ml medium in a 100 ml conical flask). The complete medium CgIII was used as the medium for the preculture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |

The pH was brought to pH 7.4.

Tetracycline (5 mg/l) was added to this. The preculture was incubated for 16 hours at 33° C. at 240 rpm on a shaking machine. A main culture was seeded from this preculture such that the initial OD (660 nm) of the main culture was 0.1. Medium MM was used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine*HCl (sterile-filtered) | 0.2 mg/l |
| L-Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Culturing was carried out in a 10 ml volume in a 100 ml conical flask with baffles. Tetracycline (5 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of threonine formed was determined with an amino acid analyzer from Eppendorf-BioTronik (Hamburg, Germany) by ion exchange chromatography and post-column derivation with ninhydrin detection.

The result of the experiment is shown in Table 1.

TABLE 1

| Strain | OD (660 nm) | L-Threonine g/l |
|---|---|---|
| DSM5399 | 12.3 | 0.74 |
| DSM5399/pECzwfopcA | 9.9 | 1.0 |

EXAMPLE 11

Preparation of L-lysine

The *C. glutamicum* strain DSM5715/pECzwfopcA obtained in Example 9 was cultured in a nutrient medium suitable for the production of lysine and the lysine content in the culture supernatant was determined.

For this, the strain was first incubated on an agar plate with the corresponding antibiotic (brain-heart agar with tetracycline (5 mg/l)) for 24 hours at 33° C. Starting from this agar plate culture, a preculture was seeded (10 ml medium in a 100 ml conical flask). The complete medium CgIII was used as the medium for the preculture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |

The pH was brought to pH 7.4.

Tetracycline (5 mg/l) was added to this. The preculture was incubated for 16 hours at 33° C. at 240 rpm on a shaking machine. A main culture was seeded from this preculture such that the initial OD (660 nm) of the main culture was 0.1 Medium MM was used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 58 g/l |
| $(NH_4)_2SO_4$ | 25 g/l |
| $KH_2PO_4$ | 0.1 g/l |
| $MgSO_4*7\ H_2O$ | 1.0 g/l |
| $CaCl_2*2\ H_2O$ | 10 mg/l |
| $FeSO_4*7\ H_2O$ | 10 mg/l |
| $MnSO_4*H_2O$ | 5.0 mg/l |
| Biotin (sterile-filtered) | 0.3 mg/l |
| Thiamine*HCl (sterile-filtered) | 0.2 mg/l |
| L-Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Culturing was carried out in a 10 ml volume in a 100 ml conical flask with baffles. Tetracycline (5 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, München). The amount of lysine formed was determined with an amino acid analyzer from Eppendorf-BioTronik (Hamburg, Germany) by ion exchange chromatography and post-column derivation with ninhydrin detection.

The result of the experiment is shown in Table 2.

TABLE 2

| Strain | OD (660 nm) | L-Lysine HCl g/l |
|---|---|---|
| DSM5715 | 10.8 | 16.0 |
| DSM5715/pECzwfopcA | 8.1 | 17.1 |

What is claimed is:

1. A process for the fermentative production of L-lysine or L-threonine, comprising the steps of:
   (a) fermentation of a *coryneform bacterium* strain producing L-lysine or L-threonine, in which at least an opcA gene comprising a nucleotide sequence which encodes the polypeptide of SEQ ID NO:3 is overexpressed by increasing the copy number of said gene or operatively linking said gene to a promoter;
   (b) enrichment of the L-lysine or L-threonine in the medium or in the *coryneform bacterium* strain; and
   (c) isolation of L-lysine or L-threonine.

2. The process according to claim 1, wherein the opcA gene comprises the nucleotide sequence of SEQ ID NO: 4.

3. The process according to claim 2, wherein a zwf gene comprising a nucleotide sequence which encodes the polypeptide of SEQ ID NO:7 is simultaneously overexpressed by increasing the copy number of said gene or operatively linking said gene to a promoter.

4. The process according to claim 3, wherein the zwf gene comprises nucleotides 115-1659 of SEQ ID NO: 6.

5. The process according to claim 4, wherein a *C. glutamicum* or *Brevibacterium* devB gene is simultaneously overexpressed by increasing the copy number of said gene or operatively linking said gene to a promoter.

6. The process according to claim 4, wherein a *C. glutamicum* or *Brevibacterium* tkt gene is simultaneously overexpressed by increasing the copy number of said gene or operatively linking said gene to a promoter.

7. The process according to claim 4, wherein one or more *C. glutamicum* genes chosen from the group consisting of:
   (a) the dapA gene which codes for dihydrodipicolinate synthase,
   (b) the lysC gene which codes for a feed back resistant aspartate kinase,
   (c) the gap gene which codes for glycerolaldehyde 3-phosphate dehydrogenase,
   (d) the pyc gene which codes for pyruvate carboxylase,
   (e) the gnd gene which codes for 6-phosphogluconate dehydrogenase,
   (f) the lysE gene which codes for lysine export protein,
   (g) the zwa1 gene,
   (h) the eno gene which codes for enolase, and
   (i) the tal gene which codes for transaldolase,
   are overexpressed by increasing the copy number of said gene or operatively linking said gene to a promoter.

8. The process according to claim 4, wherein the *coryneform bacterium* strain is *C. glutamicum*, and wherein one or more *C. glutamicum* genes selected from the group consisting of:
   (a) the pck gene which codes for phosphoenol pyruvate carboxykinase;
   (b) the pgi gene which codes for glucose 6-phosphate isomerase;
   (c) the poxB gene which codes for pyruvate oxidase; and
   (d) the zwa2 gene
   are inactivated by mutation of the coding sequence of the gene.

9. A process for the fermentative production of L-lysine or L-threonine comprising the steps of:
  (a) fermentation of a *coryneform bacterium* strain producing L-lysine or L-threonine, in which a *Corynebacterium glutamicum* opcA gene and a *Corynebacterium glutamicum* zwf gene are overexpressed by increasing the copy number of said genes or operatively linking said genes to a promoter;
  (b) enrichment of the L-lysine or L-threonine in the medium or in the *coryneform bacterium* strain; and
  (c) isolation of L-lysine or L-threonine
  wherein said *coryneform bacterium* strain is *Brevibacterium flavum*, which is deposited under deposit number DSM5399, and which is transformed with the plasmid vector pECzwfopcA, which is deposited under deposit number DSM13264.

10. The process according to claim 9, wherein a *C. glutamicum* or *Brevibacterium* devB gene is simultaneously overexpressed by increasing the copy number of said gene or operatively linking said gene to a promoter.

11. The process according to claim 9, wherein a *C. glutamicum* or *Brevibacterium* tkt gene is simultaneously overexpressed by increasing the copy number of said gene or operatively linking said gene to a promoter.

12. A process for the fermentative production of L-lysine or L-threonine comprising the steps of:
  (a) fermentation of a *coryneform bacterium* strain producing L-lysine or L-threonine, in which a *Corynebacterium glutamicum* opcA gene and a *Corynebacterium glutamicum* zwf gene are overexpressed by increasing the copy number of said genes or operatively linking said genes to a promoter;
  (b) enrichment of the L-lysine or L-threonine in the medium or in the *coryneform bacterium* strain; and
  (c) isolation of L-lysine or L-threonine
  wherein said *coryneform bacterium* strain is *Corynebacterium glutamicum*, which is deposited under deposit number DSM5715, and which is transformed with the plasmid vector pECzwfopcA, which is deposited under deposit number DSM13264.

13. The process according to claim 12, wherein a *C. glutamicum* or *Brevibacterium* devB gene is simultaneously overexpressed by increasing the copy number of said gene or operatively linking said gene to a promoter.

14. The process according to claim 12, wherein a *C. glutamicum* or *Brevibacterium* tkt gene is simultaneously overexpressed by increasing the copy number of said gene or operatively linking said gene to a promoter.

15. A process for the fermentative production of L-isoleucine or L-tryptophan, comprising the steps of:
  (a) fermentation of a *coryneform bacterium* strain producing L-isoleucine or L-tryptophan, in which at least an opcA gene comprising a nucleotide sequence which encodes the polypeptide of SEQ ID NO:3 is overexpressed by increasing the copy number of said gene or operatively linking said gene to a promoter;
  (b) enrichment of the L-isoleucine or L-tryptophan in the medium or in the *coryneform bacterium* strain; and
  (c) isolation of L-isoleucine or L-tryptophan.

16. The process according to claim 15, wherein the opcA gene comprises the nucleotide sequence of SEQ ID NO: 4.

17. The process according to claim 16, wherein a zwf gene comprising a nucleotide sequence which encodes the polypeptide of SEQ ID NO:7 is simultaneously overexpressed by increasing the copy number of said gene or operatively linking said gene to a promoter.

18. The process according to claim 17, wherein the zwf gene comprises nucleotides 115-1659 of SEQ ID NO: 6.

19. The process according to claim 18, wherein a *C. glutamicum* or *Brevibacterium* devB gene is simultaneously overexpressed by increasing the copy number of said gene or operatively linking said gene to a promoter.

20. The process according to claim 18, wherein a *C. glutamicum* or *Brevibacterium* tkt gene is simultaneously overexpressed by increasing the copy number of said gene or operatively linking said gene to a promoter.

21. The process according to claim 18, wherein one or more *C. glutamicum* genes chosen from the group consisting of:
  (a) the dapA gene which codes for dihydrodipicolinate synthase,
  (b) the lysC gene which codes for a feed back resistant aspartate kinase,
  (c) the gap gene which codes for glycerolaldehyde 3-phosphate dehydrogenase,
  (d) the pyc gene which codes for pyruvate carboxylase,
  (e) the gnd gene which codes for 6-phosphogluconate dehydrogenase,
  (f) the lysE gene which codes for lysine export protein,
  (g) the zwa1 gene,
  (h) the eno gene which codes for enolase, and
  (i) the tal gene which codes for transaldolase
  are overexpressed by increasing the copy number of said gene or operatively linking said gene to a promoter.

22. The process according to claim 18, wherein the *coryneform bacterium* strain is *C. glutamicum*, and wherein one or more *C. glutamicum* genes selected from the group consisting of:
  (a) the pck gene which codes for phosphoenol pyruvate carboxykinase,
  (b) the pgi gene which codes for glucose 6-phosphate isomerase,
  (c) the poxB gene which codes for pyruvate oxidase and
  (d) the zwa2 gene
  are inactivated by mutation of the coding sequence of the gene.

* * * * *

UNITED STATES PATENT AND TRADEMARK OFFICE
CERTIFICATE OF CORRECTION

PATENT NO. : 7,504,242 B2  
APPLICATION NO. : 10/976768  
DATED : March 17, 2009  
INVENTOR(S) : L. K. Dunican, deceased et al.

Page 1 of 1

It is certified that error appears in the above-identified patent and that said Letters Patent is hereby corrected as shown below:

On the Title Page, Item [75] should read:

L.K. Dunican, Galway, IRELAND, Deceased  
Ashling McCormack, Westmeath, IRELAND  
Cliona Stapelton, Tipparary, IRELAND  
Kevin Burke, Galway, IRELAND  
Bernd S. Moritz, Niederzier, GERMANY  
Lothar Eggeling, Jülich, GERMANY  
Hermann Sahm, Jüllich, GERMANY  
Bettina Mockel, Bielefeld, GERMANY  
Anke Weissenborn, Tübingen, GERMANY Signed and Sealed this  
Second Day of July, 2013

Teresa Stanek Rea  
*Acting Director of the United States Patent and Trademark Office*

SEQUENCE LISTING

```
<160> NUMBER OF SEQ ID NOS: 24

<210> SEQ ID NO 1
<211> LENGTH: 6995
<212> TYPE: DNA
<213> ORGANISM: Corynebacterium glutamicum
<220> FEATURE:
<223> OTHER INFORMATION: ATCC13032
<220> FEATURE:
<221> NAME/KEY: CDS
<222> LOCATION: (3658)..(5199)
<223> OTHER INFORMATION: zwf
<220> FEATURE:
<221> NAME/KEY: CDS
<222> LOCATION: (5217)..(6173)
<223> OTHER INFORMATION: opcA

<400> SEQUENCE: 1
cacatttgaa ccacagttgg ttataaaatg ggttcaacat cactatggtt agaggtgttg      60
acgggtcaga ttaagcaaag actactttcg gggtagatca cctttgccaa atttgaacca     120
attaacctaa gtcgtagatc tgatcatcgg atctaacgaa aacgaaccaa aactttggtc     180
ccggtttaac ccaggaagga ttgaccacct tgacgctgtc acctgaactt caggcgctca     240
ctgtacgcaa ttacccctct gattggtccg atgtggacac caaggctgta gacactgttc     300
gtgtcctcgc tgcagacgct gtagaaaact gtggctccgg ccacccaggc accgcaatga     360
gcctggctcc ccttgcatac accttgtacc agcgggttat gaacgtagat ccacaggaca     420
ccaactgggc aggccgtgac cgcttcgttc tttcttgtgg ccactcctct ttgacccagt     480
acatccagct ttacttgggt ggattcggcc ttgagatgga tgacctgaag gctctgcgca     540
cctgggattc cttgacccca ggacaccctg agtaccgcca caccaagggc gttgagatca     600
ccactggccc tcttggccag ggtcttgcat ctgcagttgg tatggccatg gctgctcgtc     660
gtgagcgtgg cctattcgac ccaaccgctg ctgagggcga atcccattc gaccaccaca     720 tctacgtcat tgcttctgat ggtgacctgc aggaaggtgt cacctctgag gcatcctcca     780
tcgctggcac ccagcagctg ggcaacctca tcgtgttctg ggatgacaac cgcatctcca     840
```

```
tcgaagacaa cactgagatc gctttcaacg aggacgttgt tgctcgttac aaggcttacg    900
gctggcagac cattgaggtt gaggctggcg aggacgttgc agcaatcgaa gctgcagtgg    960
ctgaggctaa gaaggacacc aagcgaccta ccttcatccg cgttcgcacc atcatcggct   1020
tcccagctcc aactatgatg aacaccggtg ctgtgcacgg tgctgctctt ggcgcagctg   1080
aggttgcagc aaccaagact gagcttggat tcgatcctga ggctcacttc gcgatcgacg   1140
atgaggttat cgctcacacc cgctcccctcg cagagcgcgc tgcacagaag aaggctgcat   1200
ggcaggtcaa gttcgatgag tgggcagctg ccaaccctga gaacaaggct ctgttcgatc   1260
gcctgaactc ccgtgagctt ccagcgggct acgctgacga gctcccaaca tgggatgcag   1320
atgagaaggg cgtcgcaact cgtaaggctt ccgaggctgc acttcaggca ctgggcaaga   1380
cccttcctga gctgtggggc ggttccgctg acctcgcagg ttccaacaac accgtgatca   1440
agggctcccc ttccttcggc cctgagtcca tctccaccga gacctggtct gctgagcctt   1500
acggccgtaa cctgcacttc ggtatccgtg agcacgctat gggatccatc ctcaacggca   1560
tttccctcca cggtggcacc cgcccatacg gcggaacctt cctcatcttc tccgactaca   1620
tgcgtcctgc agttcgtctt gcagctctca tggagaccga cgcttactac gtctggaccc   1680
acgactccat cggtctgggc gaagatggcc caacccacca gcctgttgaa accttggctg   1740
cactgcgcgc catcccaggt ctgtccgtcc tgcgtcctgc agatgcgaac gagaccgccc   1800
aggcttgggc tgcagcactt gagtacaagg aaggccctaa gggtcttgca ctgacccgcc   1860
agaacgttcc tgttctggaa ggcaccaagg agaaggctgc tgaaggcgtt cgccgcggtg   1920
gctacgtcct ggttgagggt ccaaggaaaa ccccagatgt gatcctcatg ggctccggct   1980
ccgaggttca gcttgcagtt aacgctgcga aggctctgga agctgagggc gttgcagctc   2040
gcgttgtttc cgttccttgc atggattggt tccaggagca ggacgcagag tacatcgagt   2100
ccgttctgcc tgcagctgtg accgctcgtg tgtctgttga agctggcatc gcaatgcctt   2160
ggtaccgctt cttgggcacc cagggccgtg ctgtctccct tgagcacttc ggtgcttctg   2220
cggattacca gaccctgttt gagaagttcg gcatcaccac cgatgcagtc gtggcagcgg   2280
ccaaggactc cattaacggt taattgccct gctgttttta gcttcaaccc ggggcaatat   2340
gattctccgg aatttttattg ccccggggttg ttgttgttaa tcggtacaaa gggtcttaag   2400
cacatccctt acttgcctgc tctccttgag cacagttcaa gaacaattct tttaaggaaa   2460
atttagtttc atgtctcaca ttgatgatct tgcacagctc ggcacttcca cttggctcga   2520
cgacctctcc cgcgagcgca ttacttccgg caatctcagc caggttattg aggaaaagtc   2580
tgtagtcggt gtcaccacca acccagctat tttcgcagca gcaatgtcca agggcgattc   2640
ctacgacgct cagatcgcag agctcaaggc cgctggcgca tctgttgacc aggctgttta   2700
cgccatgagc atcgacgacg ttcgcaatgc ttgtgatctg ttcaccggca tcttcgagtc   2760
ctccaacggc tacgacggcc gcgtgtccat cgaggttgac ccacgtatct ctgctgaccg   2820
cgacgcaacc ctggctcagg ccaaggagct gtgggcaaag gttgatcgtc aaacgtcat   2880
gatcaagatc cctgcaaccc caggttctttt gccagcaatc accgacgctt ggctgagggg   2940
catcagcgtt aacgtcacct tgatcttctc cgttgctcgc taccgcgagg tcatcgctgc   3000
gttcatcgag gcatcaagc aggctgctgc aaacggccac gacgtctcca agatccactc   3060
tgtggcttcc ttcttcgtct cccgcgtcga cgttgagatc gacaagcgcc tcgaggcaat   3120
cggatccgat gaggctttgg ctctgcgcgg caaggcagg gttgccaacg ctcagcgcgc   3180
ttacgctgtg tacaaggagc ttttcgacgc cgccgagctg cctgaaggtg ccaacactca   3240
```

-continued

```
gcgcccactg tgggcatcca ccggcgtgaa gaaccctgcg tacgctgcaa ctctttacgt    3300
ttccgagctg gctggtccaa acaccgtcaa caccatgcca gaaggcacca tcgacgcggt    3360
tctggagcag ggcaacctgc acggtgacac cctgtccaac tccgcggcag aagctgacgc    3420
tgtgttctcc cagcttgagg ctctgggcgt tgacttggca gatgtcttcc aggtcctgga    3480
gaccgagggt gtggacaagt tcgttgcttc ttggagcgaa ctgcttgagt ccatggaagc    3540
tcgcctgaag tagaatcagc acgctgcatc agtaacggcg acatgaaatc gaattagttc    3600
gatcttatgt ggccgttaca catctttcat taaagaaagg atcgtgacac taccatc       3657
```

```
gtg agc aca aac acg acc ccc tcc agc tgg aca aac cca ctg cgc gac    3705
Met Ser Thr Asn Thr Thr Pro Ser Ser Trp Thr Asn Pro Leu Arg Asp
 1               5                  10                  15 ccg cag gat aaa cga ctc ccc cgc atc gct ggc cct tcc ggc atg gtg    3753
Pro Gln Asp Lys Arg Leu Pro Arg Ile Ala Gly Pro Ser Gly Met Val
             20                  25                  30 atc ttc ggt gtc act ggc gac ttg gct cga aag aag ctg ctc ccc gcc    3801
Ile Phe Gly Val Thr Gly Asp Leu Ala Arg Lys Lys Leu Leu Pro Ala
         35                  40                  45 att tat gat cta gca aac cgc gga ttg ctg ccc cca gga ttc tcg ttg    3849
Ile Tyr Asp Leu Ala Asn Arg Gly Leu Leu Pro Pro Gly Phe Ser Leu
     50                  55                  60 gta ggt tac ggc cgc cgc gaa tgg tcc aaa gaa gac ttt gaa aaa tac    3897
Val Gly Tyr Gly Arg Arg Glu Trp Ser Lys Glu Asp Phe Glu Lys Tyr
 65                  70                  75                  80 gta cgc gat gcc gca agt gct ggt gct cgt acg gaa ttc cgt gaa aat    3945
Val Arg Asp Ala Ala Ser Ala Gly Ala Arg Thr Glu Phe Arg Glu Asn
                 85                  90                  95 gtt tgg gag cgc ctc gcc gag ggt atg gaa ttt gtt cgc ggc aac ttt    3993
Val Trp Glu Arg Leu Ala Glu Gly Met Glu Phe Val Arg Gly Asn Phe
            100                 105                 110 gat gat gat gca gct ttc gac aac ctc gct gca aca ctc aag cgc atc    4041
Asp Asp Asp Ala Ala Phe Asp Asn Leu Ala Ala Thr Leu Lys Arg Ile
        115                 120                 125 gac aaa acc cgc ggc acc gcc ggc aac tgg gct tac tac ctg tcc att    4089
Asp Lys Thr Arg Gly Thr Ala Gly Asn Trp Ala Tyr Tyr Leu Ser Ile
    130                 135                 140 cca cca gat tcc ttc aca gcg gtc tgc cac cag ctg gag cgt tcc ggc    4137
Pro Pro Asp Ser Phe Thr Ala Val Cys His Gln Leu Glu Arg Ser Gly
145                 150                 155                 160 atg gct gaa tcc acc gaa gaa gca tgg cgc cgc gtg atc atc gag aag    4185
Met Ala Glu Ser Thr Glu Glu Ala Trp Arg Arg Val Ile Ile Glu Lys
                165                 170                 175 cct ttc ggc cac aac ctc gaa tcc gca cac gag ctc aac cag ctg gtc    4233
Pro Phe Gly His Asn Leu Glu Ser Ala His Glu Leu Asn Gln Leu Val
            180                 185                 190 aac gca gtc ttc cca gaa tct tct gtg ttc cgc atc gac cac tat ttg    4281
Asn Ala Val Phe Pro Glu Ser Ser Val Phe Arg Ile Asp His Tyr Leu
        195                 200                 205 ggc aag gaa aca gtt caa aac atc ctg gct ctg cgt ttt gct aac cag    4329
Gly Lys Glu Thr Val Gln Asn Ile Leu Ala Leu Arg Phe Ala Asn Gln
    210                 215                 220 ctg ttt gag cca ctg tgg aac tcc aac tac gtt gac cac gtc cag atc    4377
Leu Phe Glu Pro Leu Trp Asn Ser Asn Tyr Val Asp His Val Gln Ile
225                 230                 235                 240 acc atg gct gaa gat att ggc ttg ggt gga cgt gct ggt tac tac gac    4425
Thr Met Ala Glu Asp Ile Gly Leu Gly Gly Arg Ala Gly Tyr Tyr Asp
                245                 250                 255
```

```
ggc atc ggc gca gcc cgc gac gtc atc cag aac cac ctg atc cag ctc    4473
Gly Ile Gly Ala Ala Arg Asp Val Ile Gln Asn His Leu Ile Gln Leu
        260                 265                 270 ttg gct ctg gtt gcc atg gaa gaa cca att tct ttc gtg cca gcg cag    4521
Leu Ala Leu Val Ala Met Glu Glu Pro Ile Ser Phe Val Pro Ala Gln
            275                 280                 285 ctg cag gca gaa aag atc aag gtg ctc tct gcg aca aag ccg tgc tac    4569
Leu Gln Ala Glu Lys Ile Lys Val Leu Ser Ala Thr Lys Pro Cys Tyr
        290                 295                 300 cca ttg gat aaa acc tcc gct cgt ggt cag tac gct gcc ggt tgg cag    4617
Pro Leu Asp Lys Thr Ser Ala Arg Gly Gln Tyr Ala Ala Gly Trp Gln
305                 310                 315                 320 ggc tct gag tta gtc aag gga ctt cgc gaa gaa gat ggc ttc aac cct    4665
Gly Ser Glu Leu Val Lys Gly Leu Arg Glu Glu Asp Gly Phe Asn Pro
                325                 330                 335 gag tcc acc act gag act ttt gcg gct tgt acc tta gag atc acg tct    4713
Glu Ser Thr Thr Glu Thr Phe Ala Ala Cys Thr Leu Glu Ile Thr Ser
            340                 345                 350 cgt cgc tgg gct ggt gtg ccg ttc tac ctg cgc acc ggt aag cgt ctt    4761
Arg Arg Trp Ala Gly Val Pro Phe Tyr Leu Arg Thr Gly Lys Arg Leu
        355                 360                 365 ggt cgc cgt gtt act gag att gcc gtg gtg ttt aaa gac gca cca cac    4809
Gly Arg Arg Val Thr Glu Ile Ala Val Val Phe Lys Asp Ala Pro His
370                 375                 380 cag cct ttc gac ggc gac atg act gta tcc ctt ggc caa aac gcc atc    4857
Gln Pro Phe Asp Gly Asp Met Thr Val Ser Leu Gly Gln Asn Ala Ile
385                 390                 395                 400 gtg att cgc gtg cag cct gat gaa ggt gtg ctc atc cgc ttc ggt tcc    4905
Val Ile Arg Val Gln Pro Asp Glu Gly Val Leu Ile Arg Phe Gly Ser
                405                 410                 415 aag gtt cca ggt tct gcc atg gaa gtc cgt gac gtc aac atg gac ttc    4953
Lys Val Pro Gly Ser Ala Met Glu Val Arg Asp Val Asn Met Asp Phe
            420                 425                 430 tcc tac tca gaa tcc ttc act gaa gaa tca cct gaa gca tac gag cgc    5001
Ser Tyr Ser Glu Ser Phe Thr Glu Glu Ser Pro Glu Ala Tyr Glu Arg
        435                 440                 445 ctc att ttg gat gcg ctg tta gat gaa tcc agc ctc ttc cct acc aac    5049
Leu Ile Leu Asp Ala Leu Leu Asp Glu Ser Ser Leu Phe Pro Thr Asn
        450                 455                 460 gag gaa gtg gaa ctg agc tgg aag att ctg gat cca att ctt gaa gca    5097
Glu Glu Val Glu Leu Ser Trp Lys Ile Leu Asp Pro Ile Leu Glu Ala
465                 470                 475                 480 tgg gat gcc gat gga gaa cca gag gat tac cca gcg ggt acg tgg ggt    5145
Trp Asp Ala Asp Gly Glu Pro Glu Asp Tyr Pro Ala Gly Thr Trp Gly
                485                 490                 495 cca aag agc gct gat gaa atg ctt tcc cgc aac ggt cac acc tgg cgc    5193
Pro Lys Ser Ala Asp Glu Met Leu Ser Arg Asn Gly His Thr Trp Arg
            500                 505                 510 agg cca taa tttaggggca aaaa atg atc ttt gaa ctt ccg gat acc acc    5243
Arg Pro                        Met Ile Phe Glu Leu Pro Asp Thr Thr
                                   515                 520 acc cag caa att tcc aag acc cta act cga ctg cgt gaa tcg ggc acc    5291
Thr Gln Gln Ile Ser Lys Thr Leu Thr Arg Leu Arg Glu Ser Gly Thr
        525                 530                 535 cag gtc acc acc ggc cga gtg ctc acc ctc atc gtg gtc act gac tcc    5339
Gln Val Thr Thr Gly Arg Val Leu Thr Leu Ile Val Val Thr Asp Ser
540                 545                 550                 555 gaa agc gat gtc gct gca gtt acc gag tcc acc aat gaa gcc tcg cgc    5387
Glu Ser Asp Val Ala Ala Val Thr Glu Ser Thr Asn Glu Ala Ser Arg
                560                 565                 570
```

```
gag cac cca tct cgc gtg atc att ttg gtg gtt ggc gat aaa act gca    5435
Glu His Pro Ser Arg Val Ile Ile Leu Val Val Gly Asp Lys Thr Ala
            575                 580                 585 gaa aac aaa gtt gac gca gaa gtc cgt atc ggt ggc gac gct ggt gct    5483
Glu Asn Lys Val Asp Ala Glu Val Arg Ile Gly Gly Asp Ala Gly Ala
        590                 595                 600 tcc gag atg atc atc atg cat ctc aac gga cct gtc gct gac aag ctc    5531
Ser Glu Met Ile Ile Met His Leu Asn Gly Pro Val Ala Asp Lys Leu
    605                 610                 615 cag tat gtc gtc aca cca ctg ttg ctt cct gac acc ccc atc gtt gct    5579
Gln Tyr Val Val Thr Pro Leu Leu Leu Pro Asp Thr Pro Ile Val Ala
620                 625                 630                 635 tgg tgg cca ggt gaa tca cca aag aat cct tcc cag gac cca att gga    5627
Trp Trp Pro Gly Glu Ser Pro Lys Asn Pro Ser Gln Asp Pro Ile Gly
            640                 645                 650 cgc atc gca caa cga cgc atc act gat gct ttg tac gac cgt gat gac    5675
Arg Ile Ala Gln Arg Arg Ile Thr Asp Ala Leu Tyr Asp Arg Asp Asp
        655                 660                 665 gca cta gaa gat cgt gtt gag aac tat cac cca ggt gat acc gac atg    5723
Ala Leu Glu Asp Arg Val Glu Asn Tyr His Pro Gly Asp Thr Asp Met
    670                 675                 680 acg tgg gcg cgc ctt acc cag tgg cgg gga ctt gtt gcc tca tca ttg    5771
Thr Trp Ala Arg Leu Thr Gln Trp Arg Gly Leu Val Ala Ser Ser Leu
685                 690                 695 gat cac cca cca cac agc gaa atc act tcc gtg agg ctg acc ggt gca    5819
Asp His Pro Pro His Ser Glu Ile Thr Ser Val Arg Leu Thr Gly Ala
            700                 705                 710                 715 agc ggc agt acc tcg gtg gat ttg gct gca ggc tgg ttg gcg cgg agg    5867
Ser Gly Ser Thr Ser Val Asp Leu Ala Ala Gly Trp Leu Ala Arg Arg
        720                 725                 730 ctg aaa gtg cct gtg atc cgc gag gtg aca gat gct ccc acc gtg cca    5915
Leu Lys Val Pro Val Ile Arg Glu Val Thr Asp Ala Pro Thr Val Pro
    735                 740                 745 acc gat gag ttt ggt act cca ctg ctg gct atc cag cgc ctg gag atc    5963
Thr Asp Glu Phe Gly Thr Pro Leu Leu Ala Ile Gln Arg Leu Glu Ile
750                 755                 760 gtt cgc acc acc ggc tcg atc atc atc acc atc tat gac gct cat acc    6011
Val Arg Thr Thr Gly Ser Ile Ile Ile Thr Ile Tyr Asp Ala His Thr
            765                 770                 775 ctt cag gta gag atg ccg gaa tcc ggc aat gcc cca tcg ctg gtg gct    6059
Leu Gln Val Glu Met Pro Glu Ser Gly Asn Ala Pro Ser Leu Val Ala
780                 785                 790                 795 att ggt cgt cga agt gag tcc gac tgc ttg tct gag gag ctt cgc cac    6107
Ile Gly Arg Arg Ser Glu Ser Asp Cys Leu Ser Glu Glu Leu Arg His
            800                 805                 810 atg gat cca gat ttg ggc tac cag cac gca cta tcc ggc ttg tcc agc    6155
Met Asp Pro Asp Leu Gly Tyr Gln His Ala Leu Ser Gly Leu Ser Ser
        815                 820                 825 gtc aag ctg gaa acc gtc taaggagaaa tacaacacta tggttgatgt          6203
Val Lys Leu Glu Thr Val
    830 agtacgcgca cgcgatactg aagatttggt tgcacaggct gcctccaaat tcattgaggt   6263 tgttgaagca gcaactgcca ataatggcac cgcacaggta gtgctcaccg gtggtggcgc   6323 cggcatcaag ttgctggaaa agctcagcgt tgatgcggct gaccttgcct gggatcgcat   6383 tcatgtgttc ttcggcgatg agcgcaatgt ccctgtcagt gattctgagt ccaatgaggg   6443 ccaggctcgt gaggcactgt tgtccaaggt ttctatccct gaagccaaca ttcacggata   6503
```

-continued

```
tggtctcggc gacgtagatc ttgcagaggc agcccgcgct tacgaagctg tgttggatga    6563
attcgcacca aacggctttg atcttcacct gctcggcatg ggtggcgaag gccatatcaa    6623
ctccctgttc cctcacaccg atgcagtcaa ggaatcctcc gcaaaggtca tcgcggtgtt    6683
tgattcccct aagcctcctt cagagcgtgc aactctaacc cttcctgcgg ttcactccgc    6743
aaagcgcgtg tggttgctgg tttctggtgc ggagaaggct gaggcagctg cggcgatcgt    6803
caacggtgag cctgctgttg agtggcctgc tgctggagct accggatctg aggaaacggt    6863
attgttcttg gctgatgatg ctgcaggaaa tctctaagca gcgccagctc taacaagaag    6923
ctttaacaag aagctctaac gaaaagcact aacaaactaa tccgggtgcg aaccttcatc    6983
tgaatcgatg ga                                                         6995
```

<210> SEQ ID NO 2
<211> LENGTH: 514
<212> TYPE: PRT
<213> ORGANISM: Corynebacterium glutamicum
<220> FEATURE:
<223> OTHER INFORMATION: ATCC13032

<400> SEQUENCE: 2

```
Met Ser Thr Asn Thr Thr Pro Ser Ser Trp Thr Asn Pro Leu Arg Asp
  1               5                  10                  15

Pro Gln Asp Lys Arg Leu Pro Arg Ile Ala Gly Pro Ser Gly Met Val
                 20                  25                  30

Ile Phe Gly Val Thr Gly Asp Leu Ala Arg Lys Lys Leu Leu Pro Ala
             35                  40                  45

Ile Tyr Asp Leu Ala Asn Arg Gly Leu Leu Pro Pro Gly Phe Ser Leu
         50                  55                  60

Val Gly Tyr Gly Arg Arg Glu Trp Ser Lys Glu Asp Phe Glu Lys Tyr
 65                  70                  75                  80

Val Arg Asp Ala Ala Ser Ala Gly Ala Arg Thr Glu Phe Arg Glu Asn
                 85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125

Asp Lys Thr Arg Gly Thr Ala Gly Asn Trp Ala Tyr Tyr Leu Ser Ile
    130                 135                 140

Pro Pro Asp Ser Phe Thr Ala Val Cys His Gln Leu Glu Arg Ser Gly
145                 150                 155                 160

Met Ala Glu Ser Thr Glu Glu Ala Trp Arg Arg Val Ile Ile Glu Lys
                165                 170                 175

Pro Phe Gly His Asn Leu Glu Ser Ala His Glu Leu Asn Gln Leu Val
            180                 185                 190

Asn Ala Val Phe Pro Glu Ser Ser Val Phe Arg Ile Asp His Tyr Leu
        195                 200                 205

Gly Lys Glu Thr Val Gln Asn Ile Leu Ala Leu Arg Phe Ala Asn Gln
    210                 215                 220

Leu Phe Glu Pro Leu Trp Asn Ser Asn Tyr Val Asp His Val Gln Ile
225                 230                 235                 240

Thr Met Ala Glu Asp Ile Gly Leu Gly Gly Arg Ala Gly Tyr Tyr Asp
                245                 250                 255

Gly Ile Gly Ala Ala Arg Asp Val Ile Gln Asn His Leu Ile Gln Leu
            260                 265                 270
```

```
Leu Ala Leu Val Ala Met Glu Glu Pro Ile Ser Phe Val Pro Ala Gln
            275                 280                 285

Leu Gln Ala Glu Lys Ile Lys Val Leu Ser Ala Thr Lys Pro Cys Tyr
        290                 295                 300

Pro Leu Asp Lys Thr Ser Ala Arg Gly Gln Tyr Ala Ala Gly Trp Gln
305                 310                 315                 320

Gly Ser Glu Leu Val Lys Gly Leu Arg Glu Glu Asp Gly Phe Asn Pro
                325                 330                 335

Glu Ser Thr Thr Glu Thr Phe Ala Ala Cys Thr Leu Glu Ile Thr Ser
            340                 345                 350

Arg Arg Trp Ala Gly Val Pro Phe Tyr Leu Arg Thr Gly Lys Arg Leu
        355                 360                 365

Gly Arg Arg Val Thr Glu Ile Ala Val Val Phe Lys Asp Ala Pro His
    370                 375                 380

Gln Pro Phe Asp Gly Asp Met Thr Val Ser Leu Gly Gln Asn Ala Ile
385                 390                 395                 400

Val Ile Arg Val Gln Pro Asp Glu Gly Val Leu Ile Arg Phe Gly Ser
                405                 410                 415

Lys Val Pro Gly Ser Ala Met Glu Val Arg Asp Val Asn Met Asp Phe
            420                 425                 430

Ser Tyr Ser Glu Ser Phe Thr Glu Glu Ser Pro Glu Ala Tyr Glu Arg
        435                 440                 445

Leu Ile Leu Asp Ala Leu Leu Asp Glu Ser Ser Leu Phe Pro Thr Asn
    450                 455                 460

Glu Glu Val Glu Leu Ser Trp Lys Ile Leu Asp Pro Ile Leu Glu Ala
465                 470                 475                 480

Trp Asp Ala Asp Gly Glu Pro Glu Asp Tyr Pro Ala Gly Thr Trp Gly
                485                 490                 495

Pro Lys Ser Ala Asp Glu Met Leu Ser Arg Asn Gly His Thr Trp Arg
            500                 505                 510

Arg Pro

<210> SEQ ID NO 3
<211> LENGTH: 319
<212> TYPE: PRT
<213> ORGANISM: Corynebacterium glutamicum
<220> FEATURE:
<223> OTHER INFORMATION: ATCC13032

<400> SEQUENCE: 3

Met Ile Phe Glu Leu Pro Asp Thr Thr Thr Gln Gln Ile Ser Lys Thr
  1               5                  10                  15

Leu Thr Arg Leu Arg Glu Ser Gly Thr Gln Val Thr Thr Gly Arg Val
            20                  25                  30

Leu Thr Leu Ile Val Val Thr Asp Ser Glu Ser Asp Val Ala Ala Val
        35                  40                  45

Thr Glu Ser Thr Asn Glu Ala Ser Arg Glu His Pro Ser Arg Val Ile
    50                  55                  60

Ile Leu Val Val Gly Asp Lys Thr Ala Glu Asn Lys Val Asp Ala Glu
65                  70                  75                  80

Val Arg Ile Gly Gly Asp Ala Gly Ala Ser Glu Met Ile Ile Met His
                85                  90                  95

Leu Asn Gly Pro Val Ala Asp Lys Leu Gln Tyr Val Val Thr Pro Leu
            100                 105                 110

Leu Leu Pro Asp Thr Pro Ile Val Ala Trp Trp Pro Gly Glu Ser Pro
```

```
                115                 120                 125
Lys Asn Pro Ser Gln Asp Pro Ile Gly Arg Ile Ala Gln Arg Arg Ile
            130                 135                 140

Thr Asp Ala Leu Tyr Asp Arg Asp Ala Leu Glu Asp Arg Val Glu
145                 150                 155                 160

Asn Tyr His Pro Gly Asp Thr Asp Met Thr Trp Ala Arg Leu Thr Gln
                165                 170                 175

Trp Arg Gly Leu Val Ala Ser Ser Leu Asp His Pro Pro His Ser Glu
            180                 185                 190

Ile Thr Ser Val Arg Leu Thr Gly Ala Ser Gly Ser Thr Ser Val Asp
                195                 200                 205

Leu Ala Ala Gly Trp Leu Ala Arg Arg Leu Lys Val Pro Val Ile Arg
            210                 215                 220

Glu Val Thr Asp Ala Pro Thr Val Pro Thr Asp Glu Phe Gly Thr Pro
225                 230                 235                 240

Leu Leu Ala Ile Gln Arg Leu Glu Ile Val Arg Thr Thr Gly Ser Ile
                245                 250                 255

Ile Ile Thr Ile Tyr Asp Ala His Thr Leu Gln Val Glu Met Pro Glu
            260                 265                 270

Ser Gly Asn Ala Pro Ser Leu Val Ala Ile Gly Arg Arg Ser Glu Ser
            275                 280                 285

Asp Cys Leu Ser Glu Glu Leu Arg His Met Asp Pro Asp Leu Gly Tyr
            290                 295                 300

Gln His Ala Leu Ser Gly Leu Ser Ser Val Lys Leu Glu Thr Val
305                 310                 315

<210> SEQ ID NO 4
<211> LENGTH: 960
<212> TYPE: DNA
<213> ORGANISM: Corynebacterium glutamicum
<220> FEATURE:
<223> OTHER INFORMATION: ATCC13032
<220> FEATURE:
<221> NAME/KEY: CDS
<222> LOCATION: (1)..(957)
<223> OTHER INFORMATION: opcA

<400> SEQUENCE: 4 atg atc ttt gaa ctt ccg gat acc acc acc cag caa att tcc aag acc    48
Met Ile Phe Glu Leu Pro Asp Thr Thr Thr Gln Gln Ile Ser Lys Thr
  1               5                  10                  15 cta act cga ctg cgt gaa tcg ggc acc cag gtc acc acc ggc cga gtg    96
Leu Thr Arg Leu Arg Glu Ser Gly Thr Gln Val Thr Thr Gly Arg Val
             20                  25                  30 ctc acc ctc atc gtg gtc act gac tcc gaa agc gat gtc gct gca gtt   144
Leu Thr Leu Ile Val Val Thr Asp Ser Glu Ser Asp Val Ala Ala Val
         35                  40                  45 acc gag tcc acc aat gaa gcc tcg cgc gag cac cca tct cgc gtg atc   192
Thr Glu Ser Thr Asn Glu Ala Ser Arg Glu His Pro Ser Arg Val Ile
     50                  55                  60 att ttg gtg gtt ggc gat aaa act gca gaa aac aaa gtt gac gca gaa   240
Ile Leu Val Val Gly Asp Lys Thr Ala Glu Asn Lys Val Asp Ala Glu
 65                  70                  75                  80 gtc cgt atc ggt ggc gac gct ggt gct tcc gag atg atc atc atg cat   288
Val Arg Ile Gly Gly Asp Ala Gly Ala Ser Glu Met Ile Ile Met His
                 85                  90                  95 ctc aac gga cct gtc gct gac aag ctc cag tat gtc gtc aca cca ctg   336
Leu Asn Gly Pro Val Ala Asp Lys Leu Gln Tyr Val Val Thr Pro Leu
            100                 105                 110
```

```
ttg ctt cct gac acc ccc atc gtt gct tgg tgg cca ggt gaa tca cca       384
Leu Leu Pro Asp Thr Pro Ile Val Ala Trp Trp Pro Gly Glu Ser Pro
        115                 120                 125 aag aat cct tcc cag gac cca att gga cgc atc gca caa cga cgc atc       432
Lys Asn Pro Ser Gln Asp Pro Ile Gly Arg Ile Ala Gln Arg Arg Ile
130                 135                 140 act gat gct ttg tac gac cgt gat gac gca cta gaa gat cgt gtt gag       480
Thr Asp Ala Leu Tyr Asp Arg Asp Asp Ala Leu Glu Asp Arg Val Glu
145                 150                 155                 160 aac tat cac cca ggt gat acc gac atg acg tgg gcg cgc ctt acc cag       528
Asn Tyr His Pro Gly Asp Thr Asp Met Thr Trp Ala Arg Leu Thr Gln
                165                 170                 175 tgg cgg gga ctt gtt gcc tcc tca ttg gat cac cca cca cac agc gaa       576
Trp Arg Gly Leu Val Ala Ser Ser Leu Asp His Pro Pro His Ser Glu
            180                 185                 190 atc act tcc gtg agg ctg acc ggt gca agc ggc agt acc tcg gtg gat       624
Ile Thr Ser Val Arg Leu Thr Gly Ala Ser Gly Ser Thr Ser Val Asp
        195                 200                 205 ttg gct gca ggc tgg ttg gcg cgg agg ctg aaa gtg cct gtg atc cgc       672
Leu Ala Ala Gly Trp Leu Ala Arg Arg Leu Lys Val Pro Val Ile Arg
210                 215                 220 gag gtg aca gat gct ccc acc gtg cca acc gat gag ttt ggt act cca       720
Glu Val Thr Asp Ala Pro Thr Val Pro Thr Asp Glu Phe Gly Thr Pro
225                 230                 235                 240 ctg ctg gct atc cag cgc ctg gag atc gtt cgc acc acc ggc tcg atc       768
Leu Leu Ala Ile Gln Arg Leu Glu Ile Val Arg Thr Thr Gly Ser Ile
                245                 250                 255 atc atc acc atc tat gac gct cat acc ctt cag gta gag atg ccg gaa       816
Ile Ile Thr Ile Tyr Asp Ala His Thr Leu Gln Val Glu Met Pro Glu
            260                 265                 270 tcc ggc aat gcc cca tcg ctg gtg gct att ggt cgt cga agt gag tcc       864
Ser Gly Asn Ala Pro Ser Leu Val Ala Ile Gly Arg Arg Ser Glu Ser
        275                 280                 285 gac tgc ttg tct gag gag ctt cgc cac atg gat cca gat ttg ggc tac       912
Asp Cys Leu Ser Glu Glu Leu Arg His Met Asp Pro Asp Leu Gly Tyr
290                 295                 300 cag cac gca cta tcc ggc ttg tcc agc gtc aag ctg gaa acc gtc taa       960
Gln His Ala Leu Ser Gly Leu Ser Ser Val Lys Leu Glu Thr Val
305                 310                 315

<210> SEQ ID NO 5
<211> LENGTH: 319
<212> TYPE: PRT
<213> ORGANISM: Corynebacterium glutamicum
<220> FEATURE:
<223> OTHER INFORMATION: ATCC13032

<400> SEQUENCE: 5

Met Ile Phe Glu Leu Pro Asp Thr Thr Thr Gln Gln Ile Ser Lys Thr
 1               5                  10                  15

Leu Thr Arg Leu Arg Glu Ser Gly Thr Gln Val Thr Thr Gly Arg Val
                20                  25                  30

Leu Thr Leu Ile Val Val Thr Asp Ser Glu Ser Asp Val Ala Ala Val
            35                  40                  45

Thr Glu Ser Thr Asn Glu Ala Ser Arg Glu His Pro Ser Arg Val Ile
        50                  55                  60

Ile Leu Val Val Gly Asp Lys Thr Ala Glu Asn Lys Val Asp Ala Glu
65                  70                  75                  80

Val Arg Ile Gly Gly Asp Ala Gly Ala Ser Glu Met Ile Ile Met His
```

-continued

```
                        85                  90                  95
Leu Asn Gly Pro Val Ala Asp Lys Leu Gln Tyr Val Val Thr Pro Leu
            100                 105                 110

Leu Leu Pro Asp Thr Pro Ile Val Ala Trp Trp Pro Gly Glu Ser Pro
            115                 120                 125

Lys Asn Pro Ser Gln Asp Pro Ile Gly Arg Ile Ala Gln Arg Arg Ile
            130                 135                 140

Thr Asp Ala Leu Tyr Asp Arg Asp Ala Leu Glu Asp Arg Val Glu
145                 150                 155                 160

Asn Tyr His Pro Gly Asp Thr Asp Met Thr Trp Ala Arg Leu Thr Gln
                165                 170                 175

Trp Arg Gly Leu Val Ala Ser Ser Leu Asp His Pro Pro His Ser Glu
            180                 185                 190

Ile Thr Ser Val Arg Leu Thr Gly Ala Ser Gly Ser Thr Ser Val Asp
            195                 200                 205

Leu Ala Ala Gly Trp Leu Ala Arg Arg Leu Lys Val Pro Val Ile Arg
210                 215                 220

Glu Val Thr Asp Ala Pro Thr Val Pro Thr Asp Glu Phe Gly Thr Pro
225                 230                 235                 240

Leu Leu Ala Ile Gln Arg Leu Glu Ile Val Arg Thr Thr Gly Ser Ile
            245                 250                 255

Ile Ile Thr Ile Tyr Asp Ala His Thr Leu Gln Val Glu Met Pro Glu
            260                 265                 270

Ser Gly Asn Ala Pro Ser Leu Val Ala Ile Gly Arg Arg Ser Glu Ser
            275                 280                 285

Asp Cys Leu Ser Glu Glu Leu Arg His Met Asp Pro Asp Leu Gly Tyr
            290                 295                 300

Gln His Ala Leu Ser Gly Leu Ser Ser Val Lys Leu Glu Thr Val
305                 310                 315
```

```
<210> SEQ ID NO 6
<211> LENGTH: 3038
<212> TYPE: DNA
<213> ORGANISM: Corynebacterium glutamicum AS019
<220> FEATURE:
<221> NAME/KEY: CDS
<222> LOCATION: (115)..(1656)
<223> OTHER INFORMATION: zwf
<220> FEATURE:
<221> NAME/KEY: CDS
<222> LOCATION: (1672)..(2628)
<223> OTHER INFORMATION: opcA

<400> SEQUENCE: 6
```

```
cctgaagtag aatcagcacg ctgcatcagt aacggcgaca tgaaatcgaa ttagttcgat      60
cttatgtggc cgttacacat ctttcattaa agaaaggatc gtgacactac catc gtg       117
                                                                Met
                                                                  1 agc aca aac acg acc ccc tcc agc tgg aca aac cca ctg cgc gac ccg       165
Ser Thr Asn Thr Thr Pro Ser Ser Trp Thr Asn Pro Leu Arg Asp Pro
          5                  10                  15 cag gat aaa cga ctc ccc cgc atc gct ggc cct tcc ggc atg gtg atc       213
Gln Asp Lys Arg Leu Pro Arg Ile Ala Gly Pro Ser Gly Met Val Ile
     20                  25                  30 ttc ggt gtc act ggc gac ttg gct cga aag aag ctg ctc ccc gcc att       261
Phe Gly Val Thr Gly Asp Leu Ala Arg Lys Lys Leu Leu Pro Ala Ile
 35                  40                  45 tat gat cta gca aac cgc gga ttg ctg ccc cca gga ttc tcg ttg gta       309
```

```
            Tyr Asp Leu Ala Asn Arg Gly Leu Leu Pro Pro Gly Phe Ser Leu Val
             50                  55                  60                  65 ggt tac ggc cgc cgc gaa tgg tcc aaa gaa gac ttt gaa aaa tac gta         357
Gly Tyr Gly Arg Arg Glu Trp Ser Lys Glu Asp Phe Glu Lys Tyr Val
                     70                  75                  80 cgc gat gcc gca agt gct ggt gct cgt acg gaa ttc cgt gaa aat gtt         405
Arg Asp Ala Ala Ser Ala Gly Ala Arg Thr Glu Phe Arg Glu Asn Val
                 85                  90                  95 tgg gag cgc ctc gcc gag ggt atg gaa ttt gtt cgc ggc aac ttt gat         453
Trp Glu Arg Leu Ala Glu Gly Met Glu Phe Val Arg Gly Asn Phe Asp
             100                 105                 110 gat gat gca gct ttc gac aac ctc gct gca aca ctc aag cgc atc gac         501
Asp Asp Ala Ala Phe Asp Asn Leu Ala Ala Thr Leu Lys Arg Ile Asp
         115                 120                 125 aaa acc cgc ggc acc gcc ggc aac tgg gct tac tac ctg tcc att cca         549
Lys Thr Arg Gly Thr Ala Gly Asn Trp Ala Tyr Tyr Leu Ser Ile Pro
130                 135                 140                 145 cca gat tcc ttc aca gcg gtc tgc cac cag ctg gag cgt tcc ggc atg         597
Pro Asp Ser Phe Thr Ala Val Cys His Gln Leu Glu Arg Ser Gly Met
                 150                 155                 160 gct gaa tcc acc gaa gaa gca tgg cgc cgc gtg atc atc gag aag cct         645
Ala Glu Ser Thr Glu Glu Ala Trp Arg Arg Val Ile Ile Glu Lys Pro
             165                 170                 175 ttc ggc cac aac ctc gaa tcc gca cac gag ctc aac cag ctg gtc aac         693
Phe Gly His Asn Leu Glu Ser Ala His Glu Leu Asn Gln Leu Val Asn
         180                 185                 190 gca gtc ttc cca gaa tct tct gtg ttc cgc atc gac cac tat ttg ggc         741
Ala Val Phe Pro Glu Ser Ser Val Phe Arg Ile Asp His Tyr Leu Gly
195                 200                 205 aag gaa aca gtt caa aac atc ctg gct ctg cgt ttt gct aac cag ctg         789
Lys Glu Thr Val Gln Asn Ile Leu Ala Leu Arg Phe Ala Asn Gln Leu
210                 215                 220                 225 ttt gag cca ctg tgg aac tcc aac tac gtt gac cac gtc cag atc acc         837
Phe Glu Pro Leu Trp Asn Ser Asn Tyr Val Asp His Val Gln Ile Thr
                 230                 235                 240 atg gct gaa gat att ggc ttg ggt gga cgt gct ggt tac tac gac ggc         885
Met Ala Glu Asp Ile Gly Leu Gly Gly Arg Ala Gly Tyr Tyr Asp Gly
             245                 250                 255 atc ggc gca ccg cgc gac gtc atc cag aac cac ctg atc cag ctc ttg         933
Ile Gly Ala Pro Arg Asp Val Ile Gln Asn His Leu Ile Gln Leu Leu
         260                 265                 270 gct ctg gtt gcc atg gaa gaa cca att tct ttc gtg cca gcg gca cgg         981
Ala Leu Val Ala Met Glu Glu Pro Ile Ser Phe Val Pro Ala Ala Arg
275                 280                 285 cag gca gaa aag atc aag gtg ctc tct gcg aca aag ccg tgc tac cca        1029
Gln Ala Glu Lys Ile Lys Val Leu Ser Ala Thr Lys Pro Cys Tyr Pro
290                 295                 300                 305 ttg gat aaa acc tcc gct cgt ggt cag tac gct gcc ggt tgg cag ggc        1077
Leu Asp Lys Thr Ser Ala Arg Gly Gln Tyr Ala Ala Gly Trp Gln Gly
                 310                 315                 320 tct gag tta gtc aag gga ctt cgc gaa gaa gat ggc ttc aac cct gag        1125
Ser Glu Leu Val Lys Gly Leu Arg Glu Glu Asp Gly Phe Asn Pro Glu
             325                 330                 335 tcc acc act gag act ttt gcg gct tgt acc tta gag atc acg tct cgt        1173
Ser Thr Thr Glu Thr Phe Ala Ala Cys Thr Leu Glu Ile Thr Ser Arg
         340                 345                 350 cgc tgg gct ggt gtg ccg ttc tac ctg cgc acc ggt aag cgt ctt ggt        1221
Arg Trp Ala Gly Val Pro Phe Tyr Leu Arg Thr Gly Lys Arg Leu Gly
355                 360                 365
```

```
                                                      -continued cgc cgt gtt act gag att gcc gtg gtg ttt aaa gac gca cca cac cag    1269
Arg Arg Val Thr Glu Ile Ala Val Val Phe Lys Asp Ala Pro His Gln
370                 375                 380                 385 cct ttc gac ggc gac atg act gta tcc ctt ggc caa aac gcc atc gtg    1317
Pro Phe Asp Gly Asp Met Thr Val Ser Leu Gly Gln Asn Ala Ile Val
                390                 395                 400 att cgc gtg cag cct gat gaa ggt gtg ctc atc cgc ttc ggt tcc aag    1365
Ile Arg Val Gln Pro Asp Glu Gly Val Leu Ile Arg Phe Gly Ser Lys
            405                 410                 415 gtt cca ggt tct gcc atg gaa gtc cgt gac gtc aac atg gac ttc tcc    1413
Val Pro Gly Ser Ala Met Glu Val Arg Asp Val Asn Met Asp Phe Ser
        420                 425                 430 tac tca gaa tcc ttc act gaa gaa tca cct gaa gca tac gag cgc ctc    1461
Tyr Ser Glu Ser Phe Thr Glu Glu Ser Pro Glu Ala Tyr Glu Arg Leu
    435                 440                 445 att ttg gat gcg ctg tta gat gaa tcc agc ctc ttc cct acc aac gag    1509
Ile Leu Asp Ala Leu Leu Asp Glu Ser Ser Leu Phe Pro Thr Asn Glu
450                 455                 460                 465 gaa gtg gaa ctg agc tgg aag att ctg gat cca att ctt gaa gca tgg    1557
Glu Val Glu Leu Ser Trp Lys Ile Leu Asp Pro Ile Leu Glu Ala Trp
                470                 475                 480 gat gcc gat gga gaa cca gag gat tac cca gcg ggt acg tgg ggt cca    1605
Asp Ala Asp Gly Glu Pro Glu Asp Tyr Pro Ala Gly Thr Trp Gly Pro
            485                 490                 495 aag agc gct gat gaa atg ctt tcc cgc aac ggt cac acc tgg cgc agg    1653
Lys Ser Ala Asp Glu Met Leu Ser Arg Asn Gly His Thr Trp Arg Arg
        500                 505                 510 cca taa tttaggggca aa atg atc ttt gaa ctt ccg gat acc acc acc cag  1704
Pro         Met Ile Phe Glu Leu Pro Asp Thr Thr Thr Gln
                    515                 520                 525 caa att tcc aag acc cta act cga ctg cgt gaa tcg ggc acc cag gtc    1752
Gln Ile Ser Lys Thr Leu Thr Arg Leu Arg Glu Ser Gly Thr Gln Val
                530                 535                 540 acc acc ggc cga gtg ctc acc ctc atc gtg gtc act gac tcc gaa agc    1800
Thr Thr Gly Arg Val Leu Thr Leu Ile Val Val Thr Asp Ser Glu Ser
            545                 550                 555 gat gtc gct gca gtt acc gag tcc acc aat gaa gcc tcg cgc gag cac    1848
Asp Val Ala Ala Val Thr Glu Ser Thr Asn Glu Ala Ser Arg Glu His
        560                 565                 570 cca tct cgc gtg atc att ttg gtg gtt ggc gat aaa act gca gaa aac    1896
Pro Ser Arg Val Ile Ile Leu Val Val Gly Asp Lys Thr Ala Glu Asn
575                 580                 585 aaa gtt gac gca gaa gtc cgt atc ggc ggc gac gct ggt gct tcc gag    1944
Lys Val Asp Ala Glu Val Arg Ile Gly Gly Asp Ala Gly Ala Ser Glu
590                 595                 600                 605 atg atc atc atg cat ctc aac gga cct gtc gct gac aag ctc cag tat    1992
Met Ile Ile Met His Leu Asn Gly Pro Val Ala Asp Lys Leu Gln Tyr
                610                 615                 620 gtc gtc aca cca ctg ttg ctt cct gac acc ccc atc gtt gct tgg tgg    2040
Val Val Thr Pro Leu Leu Leu Pro Asp Thr Pro Ile Val Ala Trp Trp
            625                 630                 635 cca ggt gaa tca cca aag aat cct tcc cag gac cca att gga cgc atc    2088
Pro Gly Glu Ser Pro Lys Asn Pro Ser Gln Asp Pro Ile Gly Arg Ile
        640                 645                 650 gca caa cga cgc atc act gat gct ttg tac gac cgt gat gac gca cta    2136
Ala Gln Arg Arg Ile Thr Asp Ala Leu Tyr Asp Arg Asp Asp Ala Leu
    655                 660                 665 gaa gat cgt gtt gag aac tat cac cca ggt gat acc gac atg acg tgg    2184
Glu Asp Arg Val Glu Asn Tyr His Pro Gly Asp Thr Asp Met Thr Trp
670                 675                 680                 685
```

| | | | | | | | | | | | | | | | |
|---|---|---|---|---|---|---|---|---|---|---|---|---|---|---|---|
| gcg | cgc | ctt | acc | cag | tgg | cgg | gga | ctt | gtt | gcc | tcc | tca | ttg | gat | cac | 2232 |
| Ala | Arg | Leu | Thr | Gln | Trp | Arg | Gly | Leu | Val | Ala | Ser | Ser | Leu | Asp | His |
| | | | 690 | | | | | 695 | | | | | 700 | | | cca cca cac agc gaa atc act tcc gtg agg ctg acc ggt gca agc ggc  2280
Pro Pro His Ser Glu Ile Thr Ser Val Arg Leu Thr Gly Ala Ser Gly
            705                 710                 715 agt acc tcg gtg gat ttg gct gca ggc tgg ttg gcg cgg agg ctg aaa  2328
Ser Thr Ser Val Asp Leu Ala Ala Gly Trp Leu Ala Arg Arg Leu Lys
        720                 725                 730 gtg cct gtg atc cgc gag gtg aca gat gct ccc acc gtg cca acc gat  2376
Val Pro Val Ile Arg Glu Val Thr Asp Ala Pro Thr Val Pro Thr Asp
735                 740                 745 gag ttt ggt act cca ctg ctg gct atc cag cgc ctg gag atc gtt cgc  2424
Glu Phe Gly Thr Pro Leu Leu Ala Ile Gln Arg Leu Glu Ile Val Arg
750                 755                 760                 765 acc acc ggc tcg atc atc atc acc atc tat gac gct cat acc ctt cag  2472
Thr Thr Gly Ser Ile Ile Ile Thr Ile Tyr Asp Ala His Thr Leu Gln
                770                 775                 780 gta gag atg ccg gaa tcc ggc aat gcc cca tcg ctg gtg gct att ggt  2520
Val Glu Met Pro Glu Ser Gly Asn Ala Pro Ser Leu Val Ala Ile Gly
            785                 790                 795 cgt cga agt gag tcc gac tgc ttg tct gag gag ctt cgc cac atg gat  2568
Arg Arg Ser Glu Ser Asp Cys Leu Ser Glu Glu Leu Arg His Met Asp
        800                 805                 810 cca gat ttg ggc tac cag cac gca cta tcc ggc ttg tcc agc gtc aag  2616
Pro Asp Leu Gly Tyr Gln His Ala Leu Ser Gly Leu Ser Ser Val Lys
815                 820                 825 ctg gaa acc gtc taaggagaaa tacaacacta tggttgatgt agtacgcgca      2668
Leu Glu Thr Val
830 cgcatactga agatttggtt gcacaggctg cctccaaatt cattgaggtt gttgaagcag  2728 caactgccaa taatggcacc gcacaggtag tgctcaccgg tggtggcgcc ggcatcaagt  2788 tgctggaaaa gctcagcgtt gatgcggctg accttgcctg ggatcgcatt catgtgttct  2848 tcggcgatga gcgcaatgtc cctgtcagtg attctgagtc caatgagggc caggctcgtg  2908 aggcactgtt gtccaaggtt tctatccctg aagccaacat tcacggatat ggtctcggcg  2968 acgtagatct tgcagaggca gcccgcgctt acgaagctgt gttggatgaa ttcgcaccaa  3028 acggctttga                                                       3038

```
<210> SEQ ID NO 7
<211> LENGTH: 514
<212> TYPE: PRT
<213> ORGANISM: Corynebacterium glutamicum
<220> FEATURE:
<223> OTHER INFORMATION: AS019

<400> SEQUENCE: 7
```

Met Ser Thr Asn Thr Thr Pro Ser Ser Trp Thr Asn Pro Leu Arg Asp
 1               5                  10                  15

Pro Gln Asp Lys Arg Leu Pro Arg Ile Ala Gly Pro Ser Gly Met Val
            20                  25                  30

Ile Phe Gly Val Thr Gly Asp Leu Ala Arg Lys Lys Leu Leu Pro Ala
        35                  40                  45

Ile Tyr Asp Leu Ala Asn Arg Gly Leu Leu Pro Pro Gly Phe Ser Leu
    50                  55                  60

Val Gly Tyr Gly Arg Arg Glu Trp Ser Lys Glu Asp Phe Glu Lys Tyr
65                  70                  75                  80

-continued

```
Val Arg Asp Ala Ala Ser Ala Gly Ala Arg Thr Glu Phe Arg Glu Asn
                85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125

Asp Lys Thr Arg Gly Thr Ala Gly Asn Trp Ala Tyr Tyr Leu Ser Ile
    130                 135                 140

Pro Pro Asp Ser Phe Thr Ala Val Cys His Gln Leu Glu Arg Ser Gly
145                 150                 155                 160

Met Ala Glu Ser Thr Glu Ala Trp Arg Arg Val Ile Ile Glu Lys
                165                 170                 175

Pro Phe Gly His Asn Leu Glu Ser Ala His Glu Leu Asn Gln Leu Val
            180                 185                 190

Asn Ala Val Phe Pro Glu Ser Ser Val Phe Arg Ile Asp His Tyr Leu
        195                 200                 205

Gly Lys Glu Thr Val Gln Asn Ile Leu Ala Leu Arg Phe Ala Asn Gln
    210                 215                 220

Leu Phe Glu Pro Leu Trp Asn Ser Asn Tyr Val Asp His Val Gln Ile
225                 230                 235                 240

Thr Met Ala Glu Asp Ile Gly Leu Gly Gly Arg Ala Gly Tyr Tyr Asp
                245                 250                 255

Gly Ile Gly Ala Pro Arg Asp Val Ile Gln Asn His Leu Ile Gln Leu
            260                 265                 270

Leu Ala Leu Val Ala Met Glu Glu Pro Ile Ser Phe Val Pro Ala Ala
        275                 280                 285

Arg Gln Ala Glu Lys Ile Lys Val Leu Ser Ala Thr Lys Pro Cys Tyr
    290                 295                 300

Pro Leu Asp Lys Thr Ser Ala Arg Gly Gln Tyr Ala Ala Gly Trp Gln
305                 310                 315                 320

Gly Ser Glu Leu Val Lys Gly Leu Arg Glu Glu Asp Gly Phe Asn Pro
                325                 330                 335

Glu Ser Thr Thr Glu Thr Phe Ala Ala Cys Thr Leu Glu Ile Thr Ser
            340                 345                 350

Arg Arg Trp Ala Gly Val Pro Phe Tyr Leu Arg Thr Gly Lys Arg Leu
        355                 360                 365

Gly Arg Arg Val Thr Glu Ile Ala Val Val Phe Lys Asp Ala Pro His
    370                 375                 380

Gln Pro Phe Asp Gly Asp Met Thr Val Ser Leu Gly Gln Asn Ala Ile
385                 390                 395                 400

Val Ile Arg Val Gln Pro Asp Glu Gly Val Leu Ile Arg Phe Gly Ser
                405                 410                 415

Lys Val Pro Gly Ser Ala Met Glu Val Arg Asp Val Asn Met Asp Phe
            420                 425                 430

Ser Tyr Ser Glu Ser Phe Thr Glu Glu Ser Pro Glu Ala Tyr Glu Arg
        435                 440                 445

Leu Ile Leu Asp Ala Leu Leu Asp Glu Ser Ser Leu Phe Pro Thr Asn
    450                 455                 460

Glu Glu Val Glu Leu Ser Trp Lys Ile Leu Asp Pro Ile Leu Glu Ala
465                 470                 475                 480

Trp Asp Ala Asp Gly Glu Pro Glu Asp Tyr Pro Ala Gly Thr Trp Gly
                485                 490                 495
```

Pro Lys Ser Ala Asp Glu Met Leu Ser Arg Asn Gly His Thr Trp Arg
            500                 505                 510

Arg Pro

<210> SEQ ID NO 8
<211> LENGTH: 319
<212> TYPE: PRT
<213> ORGANISM: Corynebacterium glutamicum
<220> FEATURE:
<223> OTHER INFORMATION: AS019

<400> SEQUENCE: 8

Met Ile Phe Glu Leu Pro Asp Thr Thr Thr Gln Gln Ile Ser Lys Thr
 1               5                  10                  15

Leu Thr Arg Leu Arg Glu Ser Gly Thr Gln Val Thr Thr Gly Arg Val
            20                  25                  30

Leu Thr Leu Ile Val Val Thr Asp Ser Glu Ser Asp Val Ala Ala Val
        35                  40                  45

Thr Glu Ser Thr Asn Glu Ala Ser Arg Glu His Pro Ser Arg Val Ile
    50                  55                  60

Ile Leu Val Val Gly Asp Lys Thr Ala Glu Asn Lys Val Asp Ala Glu
 65                  70                  75                  80

Val Arg Ile Gly Gly Asp Ala Gly Ala Ser Glu Met Ile Ile Met His
                85                  90                  95

Leu Asn Gly Pro Val Ala Asp Lys Leu Gln Tyr Val Val Thr Pro Leu
            100                 105                 110

Leu Leu Pro Asp Thr Pro Ile Val Ala Trp Trp Pro Gly Glu Ser Pro
        115                 120                 125

Lys Asn Pro Ser Gln Asp Pro Ile Gly Arg Ile Ala Gln Arg Arg Ile
    130                 135                 140

Thr Asp Ala Leu Tyr Asp Arg Asp Ala Leu Glu Asp Arg Val Glu
145                 150                 155                 160

Asn Tyr His Pro Gly Asp Thr Asp Met Thr Trp Ala Arg Leu Thr Gln
                165                 170                 175

Trp Arg Gly Leu Val Ala Ser Ser Leu Asp His Pro His Ser Glu
            180                 185                 190

Ile Thr Ser Val Arg Leu Thr Gly Ala Ser Gly Ser Thr Ser Val Asp
        195                 200                 205

Leu Ala Ala Gly Trp Leu Ala Arg Arg Leu Lys Val Pro Val Ile Arg
    210                 215                 220

Glu Val Thr Asp Ala Pro Thr Val Pro Thr Asp Glu Phe Gly Thr Pro
225                 230                 235                 240

Leu Leu Ala Ile Gln Arg Leu Glu Ile Val Arg Thr Thr Gly Ser Ile
                245                 250                 255

Ile Ile Thr Ile Tyr Asp Ala His Thr Leu Gln Val Glu Met Pro Glu
            260                 265                 270

Ser Gly Asn Ala Pro Ser Leu Val Ala Ile Gly Arg Arg Ser Glu Ser
        275                 280                 285

Asp Cys Leu Ser Glu Glu Leu Arg His Met Asp Pro Asp Leu Gly Tyr
    290                 295                 300

Gln His Ala Leu Ser Gly Leu Ser Ser Val Lys Leu Glu Thr Val
305                 310                 315

<210> SEQ ID NO 9
<211> LENGTH: 960
<212> TYPE: DNA

<213> ORGANISM: Corynebacterium glutamicum
<220> FEATURE:
<223> OTHER INFORMATION: AS019
<220> FEATURE:
<221> NAME/KEY: CDS
<222> LOCATION: (1)..(957)
<223> OTHER INFORMATION: opcA

<400> SEQUENCE: 9

```
atg atc ttt gaa ctt ccg gat acc acc acc cag caa att tcc aag acc      48
Met Ile Phe Glu Leu Pro Asp Thr Thr Thr Gln Gln Ile Ser Lys Thr
 1               5                  10                  15 cta act cga ctg cgt gaa tcg ggc acc cag gtc acc acc ggc cga gtg      96
Leu Thr Arg Leu Arg Glu Ser Gly Thr Gln Val Thr Thr Gly Arg Val
             20                  25                  30 ctc acc ctc atc gtg gtc act gac tcc gaa agc gat gtc gct gca gtt     144
Leu Thr Leu Ile Val Val Thr Asp Ser Glu Ser Asp Val Ala Ala Val
         35                  40                  45 acc gag tcc acc aat gaa gcc tcg cgc gag cac cca tct cgc gtg atc     192
Thr Glu Ser Thr Asn Glu Ala Ser Arg Glu His Pro Ser Arg Val Ile
     50                  55                  60 att ttg gtg gtt ggc gat aaa act gca gaa aac aaa gtt gac gca gaa     240
Ile Leu Val Val Gly Asp Lys Thr Ala Glu Asn Lys Val Asp Ala Glu
 65                  70                  75                  80 gtc cgt atc ggt ggc gac gct ggt gct tcc gag atg atc atc atg cat     288
Val Arg Ile Gly Gly Asp Ala Gly Ala Ser Glu Met Ile Ile Met His
                 85                  90                  95 ctc aac gga cct gtc gct gac aag ctc cag tat gtc gtc aca cca ctg     336
Leu Asn Gly Pro Val Ala Asp Lys Leu Gln Tyr Val Val Thr Pro Leu
            100                 105                 110 ttg ctt cct gac acc ccc atc gtt gct tgg tgg cca ggt gaa tca cca     384
Leu Leu Pro Asp Thr Pro Ile Val Ala Trp Trp Pro Gly Glu Ser Pro
        115                 120                 125 aag aat cct tcc cag gac cca att gga cgc atc gca caa cga cgc atc     432
Lys Asn Pro Ser Gln Asp Pro Ile Gly Arg Ile Ala Gln Arg Arg Ile
    130                 135                 140 act gat gct ttg tac gac cgt gat gac gca cta gaa gat cgt gtt gag     480
Thr Asp Ala Leu Tyr Asp Arg Asp Asp Ala Leu Glu Asp Arg Val Glu
145                 150                 155                 160 aac tat cac cca ggt gat acc gac atg acg tgg gcg cgc ctt acc cag     528
Asn Tyr His Pro Gly Asp Thr Asp Met Thr Trp Ala Arg Leu Thr Gln
                165                 170                 175 tgg cgg gga ctt gtt gcc tcc tca ttg gat cac cca cac agc gaa        576
Trp Arg Gly Leu Val Ala Ser Ser Leu Asp His Pro Pro His Ser Glu
            180                 185                 190 atc act tcc gtg agg ctg acc ggt gca agc ggc agt acc tcg gtg gat     624
Ile Thr Ser Val Arg Leu Thr Gly Ala Ser Gly Ser Thr Ser Val Asp
        195                 200                 205 ttg gct gca ggc tgg ttg gcg cgg agg ctg aaa gtg cct gtg atc cgc     672
Leu Ala Ala Gly Trp Leu Ala Arg Arg Leu Lys Val Pro Val Ile Arg
    210                 215                 220 gag gtg aca gat gct ccc acc gtg cca acc gat gag ttt ggt act cca     720
Glu Val Thr Asp Ala Pro Thr Val Pro Thr Asp Glu Phe Gly Thr Pro
225                 230                 235                 240 ctg ctg gct atc cag cgc ctg gag atc gtt cgc acc acc ggc tcg atc     768
Leu Leu Ala Ile Gln Arg Leu Glu Ile Val Arg Thr Thr Gly Ser Ile
                245                 250                 255 atc atc acc atc tat gac gct cat acc ctt cag gta gag atg ccg gaa     816
Ile Ile Thr Ile Tyr Asp Ala His Thr Leu Gln Val Glu Met Pro Glu
            260                 265                 270 tcc ggc aat gcc cca tcg ctg gtg gct att ggt cgt cga agt gag tcc     864
Ser Gly Asn Ala Pro Ser Leu Val Ala Ile Gly Arg Arg Ser Glu Ser
```

```
Ser Gly Asn Ala Pro Ser Leu Val Ala Ile Gly Arg Arg Ser Glu Ser
        275                 280                 285 gac tgc ttg tct gag gag ctt cgc cac atg gat cca gat ttg ggc tac      912
Asp Cys Leu Ser Glu Glu Leu Arg His Met Asp Pro Asp Leu Gly Tyr
        290                 295                 300 cag cac gca cta tcc ggc ttg tcc agc gtc aag ctg gaa acc gta taa      960
Gln His Ala Leu Ser Gly Leu Ser Ser Val Lys Leu Glu Thr Val
305                 310                 315

<210> SEQ ID NO 10
<211> LENGTH: 319
<212> TYPE: PRT
<213> ORGANISM: Corynebacterium glutamicum
<220> FEATURE:
<223> OTHER INFORMATION: AS019

<400> SEQUENCE: 10

Met Ile Phe Glu Leu Pro Asp Thr Thr Gln Gln Ile Ser Lys Thr
 1               5                  10                  15

Leu Thr Arg Leu Arg Glu Ser Gly Thr Gln Val Thr Thr Gly Arg Val
             20                  25                  30

Leu Thr Leu Ile Val Val Thr Asp Ser Glu Ser Asp Val Ala Ala Val
                 35                  40                  45

Thr Glu Ser Thr Asn Glu Ala Ser Arg Glu His Pro Ser Arg Val Ile
     50                  55                  60

Ile Leu Val Val Gly Asp Lys Thr Ala Glu Asn Lys Val Asp Ala Glu
 65                  70                  75                  80

Val Arg Ile Gly Gly Asp Ala Gly Ala Ser Glu Met Ile Ile Met His
                 85                  90                  95

Leu Asn Gly Pro Val Ala Asp Lys Leu Gln Tyr Val Val Thr Pro Leu
            100                 105                 110

Leu Leu Pro Asp Thr Pro Ile Val Ala Trp Trp Pro Gly Glu Ser Pro
        115                 120                 125

Lys Asn Pro Ser Gln Asp Pro Ile Gly Arg Ile Ala Gln Arg Arg Ile
    130                 135                 140

Thr Asp Ala Leu Tyr Asp Arg Asp Ala Leu Glu Asp Arg Val Glu
145                 150                 155                 160

Asn Tyr His Pro Gly Asp Thr Asp Met Thr Trp Ala Arg Leu Thr Gln
                165                 170                 175

Trp Arg Gly Leu Val Ala Ser Ser Leu Asp His Pro His Ser Glu
            180                 185                 190

Ile Thr Ser Val Arg Leu Thr Gly Ala Ser Gly Ser Thr Ser Val Asp
        195                 200                 205

Leu Ala Ala Gly Trp Leu Ala Arg Arg Leu Lys Val Pro Val Ile Arg
    210                 215                 220

Glu Val Thr Asp Ala Pro Thr Val Pro Thr Asp Glu Phe Gly Thr Pro
225                 230                 235                 240

Leu Leu Ala Ile Gln Arg Leu Glu Ile Val Arg Thr Thr Gly Ser Ile
                245                 250                 255

Ile Ile Thr Ile Tyr Asp Ala His Thr Leu Gln Val Glu Met Pro Glu
            260                 265                 270

Ser Gly Asn Ala Pro Ser Leu Val Ala Ile Gly Arg Arg Ser Glu Ser
        275                 280                 285

Asp Cys Leu Ser Glu Glu Leu Arg His Met Asp Pro Asp Leu Gly Tyr
    290                 295                 300

Gln His Ala Leu Ser Gly Leu Ser Ser Val Lys Leu Glu Thr Val
```

<210> SEQ ID NO 11
<211> LENGTH: 15
<212> TYPE: PRT
<213> ORGANISM: Corynebacterium glutamicum
<220> FEATURE:
<223> OTHER INFORMATION: ATCC13032
<220> FEATURE:
<221> NAME/KEY: MOD_RES
<222> LOCATION: (1)..(5)
<223> OTHER INFORMATION: Variable amino acid
<220> FEATURE:
<221> NAME/KEY: MOD_RES
<222> LOCATION: (7)..(8)
<223> OTHER INFORMATION: Variable amino acid
<220> FEATURE:
<221> NAME/KEY: MOD_RES
<222> LOCATION: (10)
<223> OTHER INFORMATION: Variable amino acid

<400> SEQUENCE: 11

Xaa Xaa Xaa Xaa Xaa Pro Xaa Xaa Trp Xaa Asn Pro Leu Arg Asp
 1               5                  10                  15

<210> SEQ ID NO 12
<211> LENGTH: 15
<212> TYPE: PRT
<213> ORGANISM: Corynebacterium glutamicum
<220> FEATURE:
<223> OTHER INFORMATION: ATCC13032
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (8)..(10)
<223> OTHER INFORMATION: Variable amino acid

<400> SEQUENCE: 12

Met Ile Phe Xaa Leu Pro Asp Xaa Xaa Xaa Gln Gln Ile Ser Lys
 1               5                  10                  15

<210> SEQ ID NO 13
<211> LENGTH: 23
<212> TYPE: DNA
<213> ORGANISM: Artificial sequence
<220> FEATURE:
<223> OTHER INFORMATION: Description of artificial sequence: Primer zwf1

<400> SEQUENCE: 13
atygaycact ayytsggyaa rga                                       23

<210> SEQ ID NO 14
<211> LENGTH: 18
<212> TYPE: DNA
<213> ORGANISM: Artificial sequence
<220> FEATURE:
<223> OTHER INFORMATION: Description of artificial sequence: Primer zwf2

<400> SEQUENCE: 14
raawggmacr ccykscca                                             18

<210> SEQ ID NO 15
<211> LENGTH: 22
<212> TYPE: DNA
<213> ORGANISM: Artificial sequence
<220> FEATURE:
<223> OTHER INFORMATION: Description of artificial sequence: Universal -continued forward primer

<400> SEQUENCE: 15
gtaatacgac tcactatagg gc                                                    22

<210> SEQ ID NO 16
<211> LENGTH: 19
<212> TYPE: DNA
<213> ORGANISM: Artificial sequence
<220> FEATURE:
<223> OTHER INFORMATION: Description of artificial sequence: M13 forward
     primer

<400> SEQUENCE: 16
ggaaacagct atgaccatg                                                       19

<210> SEQ ID NO 17
<211> LENGTH: 17
<212> TYPE: DNA
<213> ORGANISM: Artificial sequence
<220> FEATURE:
<223> OTHER INFORMATION: Description of artificial sequence: Internal
     primer 1

<400> SEQUENCE: 17
tcaaccctga gtccacc                                                           17

<210> SEQ ID NO 18
<211> LENGTH: 17
<212> TYPE: DNA
<213> ORGANISM: Artificial sequence
<220> FEATURE:
<223> OTHER INFORMATION: Description of artificial sequence: Internal
     primer 2

<400> SEQUENCE: 18
ctgaccacga gcggagg                                                           17

<210> SEQ ID NO 19
<211> LENGTH: 17
<212> TYPE: DNA
<213> ORGANISM: Artificial sequence
<220> FEATURE:
<223> OTHER INFORMATION: Description of artificial sequence: Internal
     primer 3

<400> SEQUENCE: 19
atggtgatct ggacgtg                                                           17

<210> SEQ ID NO 20
<211> LENGTH: 17
<212> TYPE: DNA
<213> ORGANISM: Artificial sequence
<220> FEATURE:
<223> OTHER INFORMATION: Description of artificial sequence: Internal
     primer 4

<400> SEQUENCE: 20
ctggcgactt ggctcga                                                           17

<210> SEQ ID NO 21
<211> LENGTH: 18
<212> TYPE: DNA
<213> ORGANISM: Artificial sequence
<220> FEATURE:
<223> OTHER INFORMATION: Description of artificial sequence: Internal
     primer 5

```
<400> SEQUENCE: 21
cttccggata ccaccacc                                                 18

<210> SEQ ID NO 22
<211> LENGTH: 21
<212> TYPE: DNA
<213> ORGANISM: Artificial sequence
<220> FEATURE:
<223> OTHER INFORMATION: Description of artificial sequence: zwf fwd.
      primer

<400> SEQUENCE: 22
agaatcagca cgctgcatca g                                             21

<210> SEQ ID NO 23
<211> LENGTH: 18
<212> TYPE: DNA
<213> ORGANISM: Artificial sequence
<220> FEATURE:
<223> OTHER INFORMATION: Description of artificial sequence: opcA rev.
      primer

<400> SEQUENCE: 23
agtatggtgc gcgtacta                                                 18

<210> SEQ ID NO 24
<211> LENGTH: 15
<212> TYPE: PRT
<213> ORGANISM: Brevibacterium flavum

<400> SEQUENCE: 24

Met Val Ile Phe Gly Val Thr Gly Asp Leu Ala Arg Lys Lys Leu
 1               5                  10                  15
```